United States Patent
Grayson et al.

(10) Patent No.: US 11,925,725 B2
(45) Date of Patent: Mar. 12, 2024

(54) EXTRACELLULAR MATRIX (ECM) MIXTURE AND ECM SCAFFOLDS MADE WITH SAME

(71) Applicant: The Johns Hopkins University, Baltimore, MD (US)

(72) Inventors: Warren Grayson, Baltimore, MD (US); Jennifer Elisseeff, Baltimore, MD (US); Ben Hung, Baltimore, MD (US); Ethan Nyberg, Sterling, VA (US); Tram Nguyen, Baltimore, MD (US)

(73) Assignee: JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/739,946

(22) PCT Filed: Jun. 24, 2016

(86) PCT No.: PCT/US2016/039293
§ 371 (c)(1),
(2) Date: Dec. 26, 2017

(87) PCT Pub. No.: WO2016/210288
PCT Pub. Date: Dec. 29, 2016

(65) Prior Publication Data
US 2018/0185547 A1    Jul. 5, 2018

Related U.S. Application Data

(60) Provisional application No. 62/183,948, filed on Jun. 24, 2015.

(51) Int. Cl.
| | |
|---|---|
| *A61L 27/36* | (2006.01) |
| *A61L 27/16* | (2006.01) |
| *A61L 27/18* | (2006.01) |
| *A61L 27/56* | (2006.01) |
| *B33Y 10/00* | (2015.01) |
| *C08L 29/04* | (2006.01) |

(52) U.S. Cl.
CPC .......... *A61L 27/3633* (2013.01); *A61L 27/16* (2013.01); *A61L 27/18* (2013.01); *A61L 27/3608* (2013.01); *A61L 27/56* (2013.01); *B33Y 10/00* (2014.12); *C08L 29/04* (2013.01)

(58) Field of Classification Search
CPC ...... A61L 27/3633; A61L 27/16; A61L 27/18; A61L 27/3608; A61L 27/56; B33Y 10/00; C08L 67/04
See application file for complete search history.

(56) References Cited

U.S. PATENT DOCUMENTS

| | | | | |
|---|---|---|---|---|
| 5,518,680 | A * | 5/1996 | Cima .................. | A61F 2/022 |
| | | | | 264/401 |
| 2004/0146543 | A1* | 7/2004 | Shimp ................. | A61L 27/3608 |
| | | | | 424/423 |
| 2007/0191963 | A1* | 8/2007 | Winterbottom ....... | A61F 2/28 |
| | | | | 623/23.5 |
| 2014/0257518 | A1 | 9/2014 | Mcalpine et al. | |
| 2015/0010510 | A1 | 1/2015 | Badylak et al. | |

FOREIGN PATENT DOCUMENTS

| | | | |
|---|---|---|---|
| WO | WO 2003030956 | 4/2003 | |
| WO | WO 2012058617 | 5/2012 | |
| WO | WO-2014190349 A2 * | 11/2014 | ............. A61L 27/58 |
| WO | WO-2015103149 A1 * | 7/2015 | ............... A61F 2/28 |

OTHER PUBLICATIONS

The University of Western Australia, Blue Histology-Skeletal Tissues-Bone, obtained online at: http://www.lab.anhb.uwa.edu.au/mb140/CorePages/Bone/Bone.htm, downloaded on Apr. 29, 2019, pp. 1-12. (Year: 2009).*
Vassilis Karageorgiou et al., Porosity of 3D biomaterial scaffolds and osteogenesis, Biomaterials, vol. 26, Issue 27, pp. 5474-5491. (Year: 2005).*
Ang et al., Compressive properties and degradability of poly(epsilon-caprolactone)/hydroxyapatite composites under accelerated hydrolytic degradation. J. Biomed. Mater. Res., Part A 2007, 80 (3), 655-60.
Azami et al., Synthesis and characterization of a laminated hydroxyapatite/gelatin nanocomposite scaffold with controlled pore structure for bone tissue engineering. Int. J. Artif. Organs 2010, 33 (2), 86-95.
Baas et al., Ceramic bone graft substitute with equine bone protein extract is comparable to allograft in terms of implant fixation: a study in dogs. Acta Orthopaedica 2008, 79 (6), 841-50.
Benzel et al., The diagnosis of infections associated with acrylic cranioplasties. Neuroradiology 1990, 32 (2), 151-3.
Bhumiratana et al., Nucleation and growth of mineralized bone matrix on silk-hydroxyapatite composite scaffolds. Biomaterials 2011, 32 (11), 2812-20.
Breeze et al., Combat-related craniofacial and cervical injuries: a 5-year review from the British military. J. Trauma 2011, 71 (1), 108-13.
Broyles et al., The fusion of craniofacial reconstruction and microsurgery: a functional and aesthetic approach. Plast. Reconstr. Surg. 2014, 134 (4), 760-9.

(Continued)

*Primary Examiner* — Abigail Vanhorn
(74) *Attorney, Agent, or Firm* — Casimir Jones, SC; Jeffrey W. Childers

(57) ABSTRACT

An extracellular matrix (ECM) mixture and ECM scaffolds made with same are disclosed. The ECM mixture can comprise from about 5% to about 85% by weight of ECM material and from about 15% to about 95% by weight of a polymer material, such as, but not limited to, a biodegradable polyester. The presently disclosed anatomically-shaped porous ECM scaffolds can be formed, for example, using a three-dimensional (3D) printing process, an injection molding process, or any other process.

15 Claims, 29 Drawing Sheets

(56) References Cited

OTHER PUBLICATIONS

Brydone et al., Bone grafting, orthopaedic biomaterials, and the clinical need for bone engineering. Proc. Inst. Mech. Eng., Part H 2011, 224 (12), 1329-43.

Correia et al., In vitro model of vascularized bone: synergizing vascular development and osteogenesis. PLoS One 2011, 6 (12), e28352.

Cowan et al., Adipose-derived adult stromal cells heal critical-size mouse calvarial defects. Nat. Biotechnol. 2004, 22 (5), 560-7.

Dalby et al., The control of human mesenchymal cell differentiation using nanoscale symmetry and disorder. Nat. Mater. 2007, 6 (12), 997-1003.

Deligianni et al., Effect of surface roughness of hydroxyapatite on human bone marrow cell adhesion, proliferation, differentiation and detachment strength. Biomaterials 2001, 22 (1), 87-96.

Desai, Osteobiologics. Am. J. Orthop. 2007, 36 (4 Suppl), 8-11.

Eshraghi et al., Mechanical and microstructural properties of polycaprolactone scaffolds with one-dimensional, two-dimensional, and three-dimensional orthogonally oriented porous architectures produced by selective laser sintering. Acta Biomater. 2010, 6 (7), 2467-76.

Estes et al., Isolation of adipose-derived stem cells and their induction to a chondrogenic phenotype. Nat. Protoc. 2010, 5 (7), 1294-1311.

Feuerstein et al., Mathematical analysis of the control of neurotransmitter release by presynaptic receptors as a supplement to experimental data. Naunyn-Schmiedeberg's Arch. Pharmacol. 1999, 359 (5), 345-59.

Gerhardt et al., Neocellularization and neovascularization of nanosized bioactive glass-coated decellularized trabecular bone scaffolds. J. Biomed. Mater. Res., Part A 2013, 101 (3), 827-41.

Goldstein, The mechanical properties of trabecular bone: dependence on anatomic location and function. J. Biomech. 1987, 20 (11-12), 1055-61.

Grayson et al., Engineering anatomically shaped human bone grafts. Proc. Natl. Acad. Sci. U. S. A. 2010, 107 (8), 3299-304.

Gupta et al., Applications of an athymic nude mouse model of nonhealing critical-sized calvarial defects. J. Craniofac. Surg. 2008, 19 (1), 192-7.

Harakas, Demineralized bone-matrix-induced osteogenesis. Clin. Orthop. Relat. Res. 1984, No. 188, 239-51.

Hung et al., Engineering bone grafts with enhanced bone marrow and native scaffolds. Cells Tissues Organs 2013, 198 (2), 87-98.

Hung et al., Mechanical control of tissue-engineered bone. Stem Cell Res. Ther. 2013, 4 (1), 10.

Hung et al., Platelet-derived growth factor BB enhances osteogenesis of adipose-derived but not bone marrow-derived mesenchymal stromal/stem cells. Stem Cells 2015, 33 (9), 2773-2784.

Hung et al., Quantitative characterization of mesenchymal stem cell adhesion to the articular cartilage surface. J. Biomed. Mater. Res., Part A 2013, 101 (12), 3592-8.

Hutton et al., Tumor Necrosis Factor improves vascularization in osteogenic grafts engineered with human adipose-derived stem/stromal cells. PLoS One 2014, 9 (9), e107199.

Iejima et al., A collagen-phosphophoryn sponge as a scaffold for bone tissue engineering. J. Biomater. Sci., Polym. Ed. 2003, 14 (10), 1097-1103.

Inzana et al., 3D printing of composite calcium phosphate and collagen scaffolds for bone regeneration. Biomaterials 2014, 35 (13), 4026-34.

Kister et al., Structural characterization and hydrolytic degradation of solid copolymers of D,L-lactide-co-epsilon-caprolactone by Raman spectroscopy. Polymer 2000, 41 (3), 925-932.

Langer et al., Tissue engineering. Science 1993, 260 (5110), 920-6.

Mandair et al., Contributions of Raman spectroscopy to the understanding of bone strength. BoneKEy Rep. 2015, 4, 620.

Marcos-Campos et al., Bone scaffold architecture modulates the development of mineralized bone matrix by human embryonic stem cells. Biomaterials 2012, 33 (33), 8329-42.

Mauney et al., In vitro and in vivo evaluation of differentially demineralized cancellous bone scaffolds combined with human bone marrow stromal cells for tissue engineering. Biomaterials 2005, 26(16), 3173-3185.

Mauney et al., Osteogenic differentiation of human bone marrow stromal cells on partially demineralized bone scaffolds in vitro. Tissue Eng. 2004, 10 (1-2), 81-92.

McNamara et al., Nanotopographical control of stem cell differentiation. J. Tissue Eng. 2010, 2010, 120623.

Nienhuijs et al., Healing of bone defects in the goat mandible, using Colloss (R) E and beta-tricalciumphosphate. J. Biomed. Mater. Res., Part B 2010, 92B (2), 517-524.

Oliveira et al., Macroporous hydroxyapatite scaffolds for bone tissue engineering applications: physicochemical characterization and assessment of rat bone marrow stromal cell viability. J. Biomed. Mater. Res., Part A 2009, 91 (1), 175-86.

Park et al., Biomechanical properties of calvarium prosthesis. Neurol. Res. 2001, 23 (2-3), 267-76.

Park et al., Scaffolds for bone tissue engineering fabricated from two different materials by the rapid prototyping technique: PCL versus Plga. J. Mater. Sci.: Mater. Med. 2012, 23 (11), 2671-8.

Parker et al., Updated National Birth Prevalence estimates for selected birth defects in the United States, 2004-2006. Birth Defects Res., Part A, 2010, 88 (12), 1008-16.

Reddy et al., Clinical outcomes in cranioplasty: risk factors and choice of reconstructive material. Plast. Reconstr. Surg. 2014, 133 (4), 864-73.

Reyes et al., A centrifugation cell adhesion assay for high-throughput screening of biomaterial surfaces. J. Biomed. Mater. Res., Part A 2003, 67 (1), 328-33.

Saito et al., Effects of designed PLLA and 50:50 PLGA scaffold architectures on bone formation in vivo. J. Tissue Eng. Regener. Med. 2013, 7 (2), 99-111.

Sampath et al., Dissociative extraction and reconstitution of extracellular matrix components involved in local bone differentiation. Proc. Natl. Acad. Sci. U. S. A. 1981, 78 (12), 7599-603.

Sathyavathi et al., Raman spectroscopic sensing of carbonate intercalation in breast microcalcifications at stereotactic biopsy. Sci. Rep. 2015, 5, 9907.

Sauermann et al., Some mathematical models for concentration-response relationships. Biom. J. 1998, 40 (7), 865-881.

Sawyer et al., The stimulation of healing within a rat calvarial defect by mPCL-TCP/collagen scaffolds loaded with rhBMP-2. Biomaterials 2009, 30 (13), 2479-2488.

Stoppato et al., Influence of scaffold pore size on collagen I development: A new in vitro evaluation perspective. J. Bioact. Compat. Polym. 2013, 28 (1), 16-32.

Suwanprateeb et al., Mechanical and in vitro performance of apatite-wollastonite glass ceramic reinforced hydroxyapatite composite fabricated by 3D-printing. J. Mater. Sci.: Mater. Med. 2009, 20 (6), 1281-1289.

Taddei et al., In vitro mineralization of bioresorbable poly(epsilon-caprolactone)/apatite composites for bone tissue engineering: a vibrational and thermal investigation. J. Mol. Struct. 2005, 744, 135-143.

Temple et al., Engineering anatomically shaped vascularized bone grafts with hASCs and 3Dprinted PCL scaffolds. J. Biomed. Mater. Res., Part A 2014, 102 (12), 4317-4325.

Ucar et al., Chitosan-based wetspun scaffolds for bioactive agent delivery. J. Appl. Polym. Sci. 2013, 130 (5), 3759-3769.

Umeda et al., Bone regeneration of canine skull using bone marrow-derived stromal cells and beta-tricalcium phosphate. Laryngoscope 2007, 117 (6), 997-1003.

Urist et al., Solubilized and insolubilized bone morphogenetic protein. Proc. Natl. Acad. Sci. U. S. A. 1979, 76 (4), 1828-32.

Urist, Bone: formation by autoinduction. Science 1965, 150 (3698), 893-9.

Wang et al., Bone morphogenetic protein-2-induced signaling and osteogenesis is regulated by cell shape, RhoA/ROCK, and cytoskeletal tension. Stem Cells Dev. 2012, 21 (7), 1176-1186.

Wei et al., Fibula osteoseptocutaneous flap for reconstruction of composite mandibular defects. Plast. Reconstr. Surg. 1994, 93 (2), 294-304.

(56) References Cited

OTHER PUBLICATIONS

Yilgor et al., Sequential BMP-2/BMP-7 delivery from polyester nanocapsules. J. Biomed. Mater. Res., Part A 2010, 93 (2), 528-36.
Zein et al., Fused deposition modeling of novel scaffold architectures for tissue engineering applications. Biomaterials 2002, 23 (4), 1169-85.
Zhou et al., In vitro bone engineering based on polycaprolactone and polycaprolactone-tricalcium phosphate composites. Polym. Int. 2007, 56 (3), 333-342.
International Search Report and Written Opinion for PCT/US2016/039293, dated Oct. 5, 2016, 11 pages.
Nyberg et al., Comparison of 3D-Printed Poly-ϵ-Caprolactone Scaffolds Functionalized with Tricalcium Phosphate, Hydroxyapatite, Bio-Oss, or Decellularized Bone Matrix. Tissue Eng Part A. Jun. 2017;23(11-12):503-514.
Singh et al., Point-of-care treatment of geometrically complex midfacial critical-sized bone defects with 3D-Printed scaffolds and autologous stromal vascular fraction. Biomaterials. Mar. 2022;282:121392.

* cited by examiner

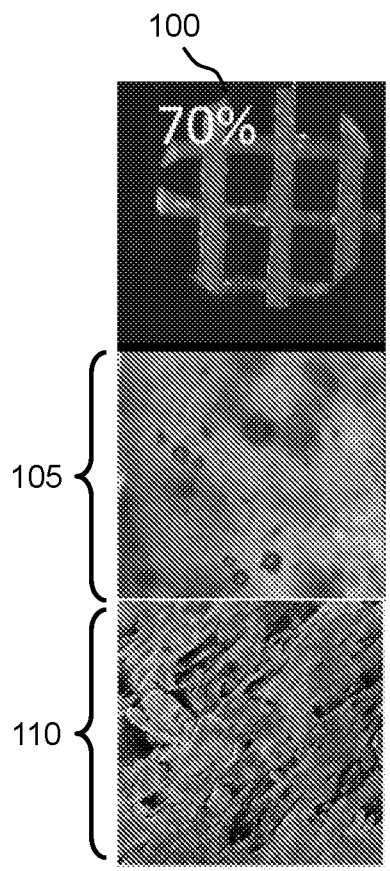
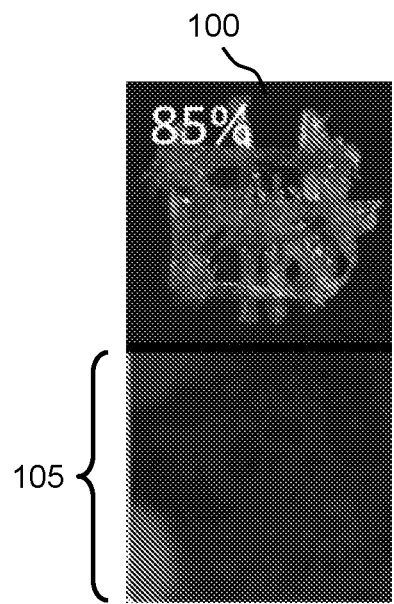
FIG. 1C
FIG. 1D

EXTRACELLULAR MATRIX (ECM) MIXTURE AND ECM SCAFFOLDS MADE WITH SAME

CROSS-REFERENCE TO RELATED APPLICATIONS

This application is a 35 U.S.C. § 371 National Stage Entry of International Application No. PCT/US16/039293 having an international filing date of Jun. 24, 2016, which claims the benefit of U.S. Provisional Application No. 62/183,948, filed Jun. 24, 2015, the contents of which are incorporated herein by reference in its their entirety.

FEDERALLY SPONSORED RESEARCH OR DEVELOPMENT

This invention was made with government support under W81XWH-11-2-0022, awarded by the Army Medical Research and Material Command. The government has certain rights in the invention.

TECHNICAL FIELD

The presently disclosed subject matter relates generally to bone repair and/or reconstruction methods and more particularly to an extracellular matrix (ECM) mixture and ECM scaffolds made with same.

BACKGROUND

Current bone scaffolds are either purely synthetic (e.g., composed of, for example, polycaprolactone) or purely natural (e.g., decellularized trabecular bone). The former is bioinert while the latter is difficult to use for the generating large, clinically sized scaffolds. Some scaffolds attempt to incorporate synthetic mineral components, such as hydroxyapatite, to increase bioactivity, but such scaffolds neglect the bioactive aspects of bone, such as the organic phase.

SUMMARY

In some aspects, the presently disclosed subject matter provides an extracellular matrix (ECM) mixture comprising from about 5% to about 85% by weight of ECM material and from about 15% to about 95% by weight of a biocompatible polymer material. In certain embodiments, the ECM mixture comprises a weight percent selected from the group consisting of from about 5% by weight ECM material and about 95% by weight biocompatible polymer material, from about 30% by weight ECM material and about 70% by weight biocompatible polymer material, from about 70% by weight ECM material and about 30% by weight biocompatible polymer material, and from about 85% by weight ECM material and about 15% by weight biocompatible polymer material.

In other aspects, the presently disclosed subject matter provides an anatomically-shaped porous extracellular matrix (ECM) scaffold comprising the presently disclosed extracellular matrix (ECM).

In yet other aspects, the presently disclosed subject matter provides an anatomically-shaped porous extracellular matrix (ECM) scaffold, the method comprising: (a) obtaining a tomography image of a subject's anatomical bone or organ; (b) providing a presently disclosed extracellular matrix (ECM) mixture; and (c) using the tomography image of step (a) to inform a manufacturing process to form an anatomically-shaped porous extracellular matrix (ECM) scaffold. In certain aspects, the manufacturing process comprises a 3D printing process. In other aspects, the manufacturing process comprises an injection molding process.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1A:
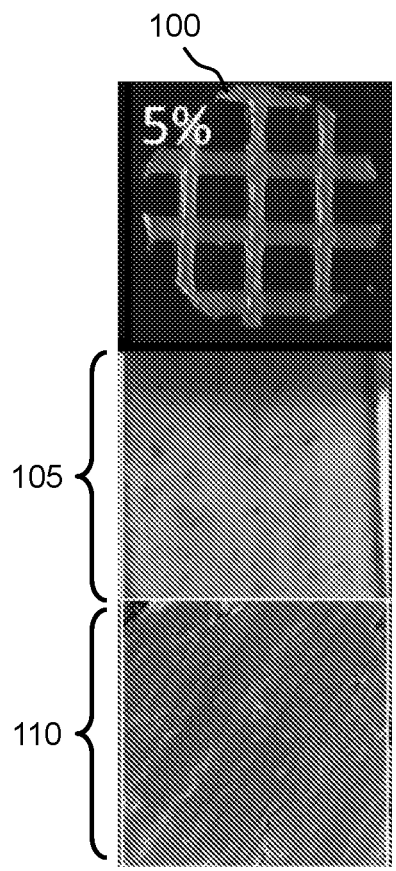
Figure 1B:
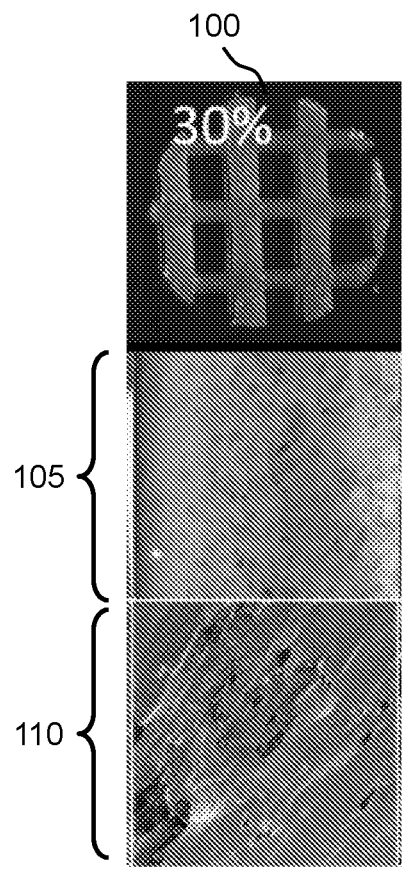
Figure 2:
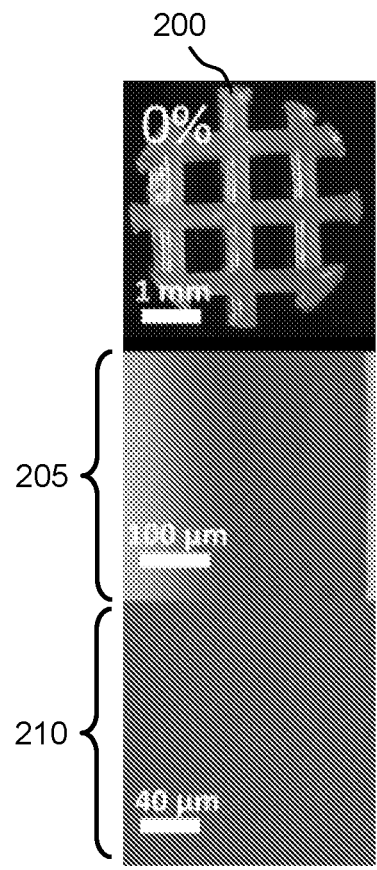
Figure 3:
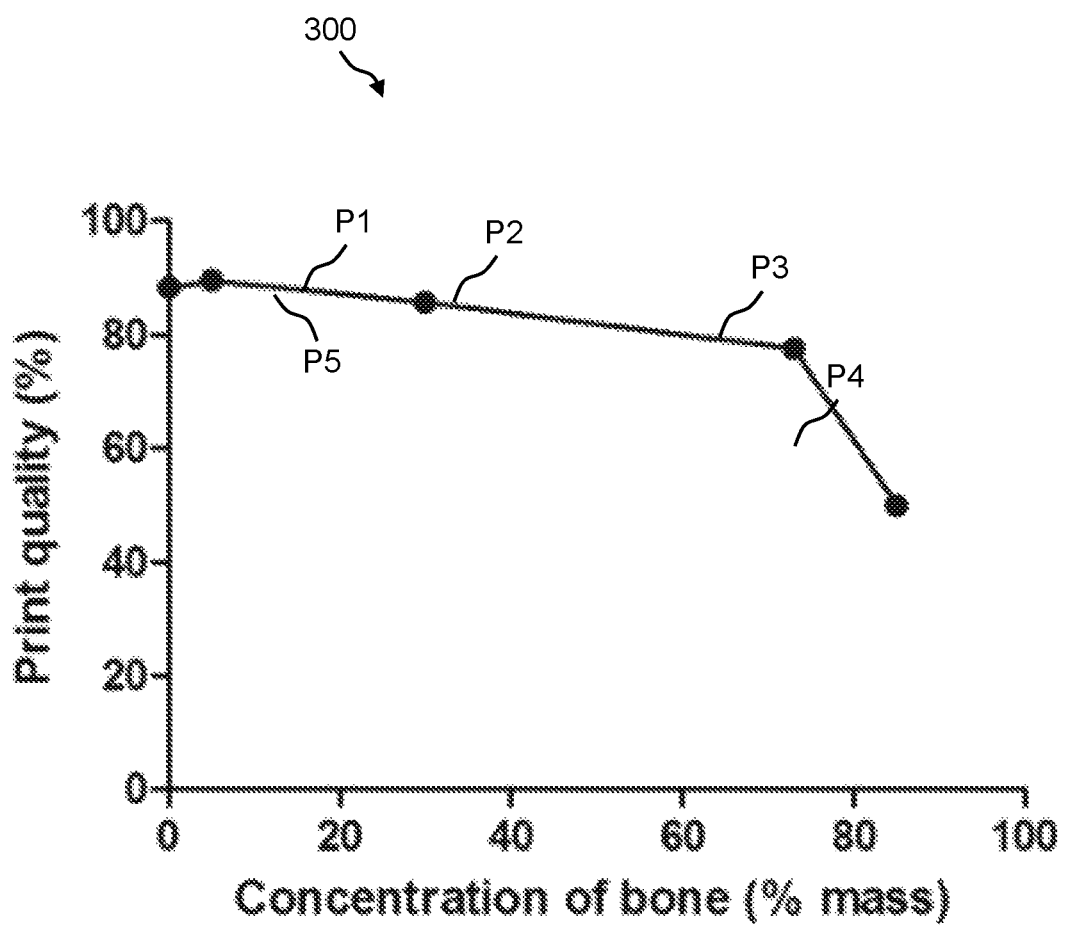
Figure 4A:
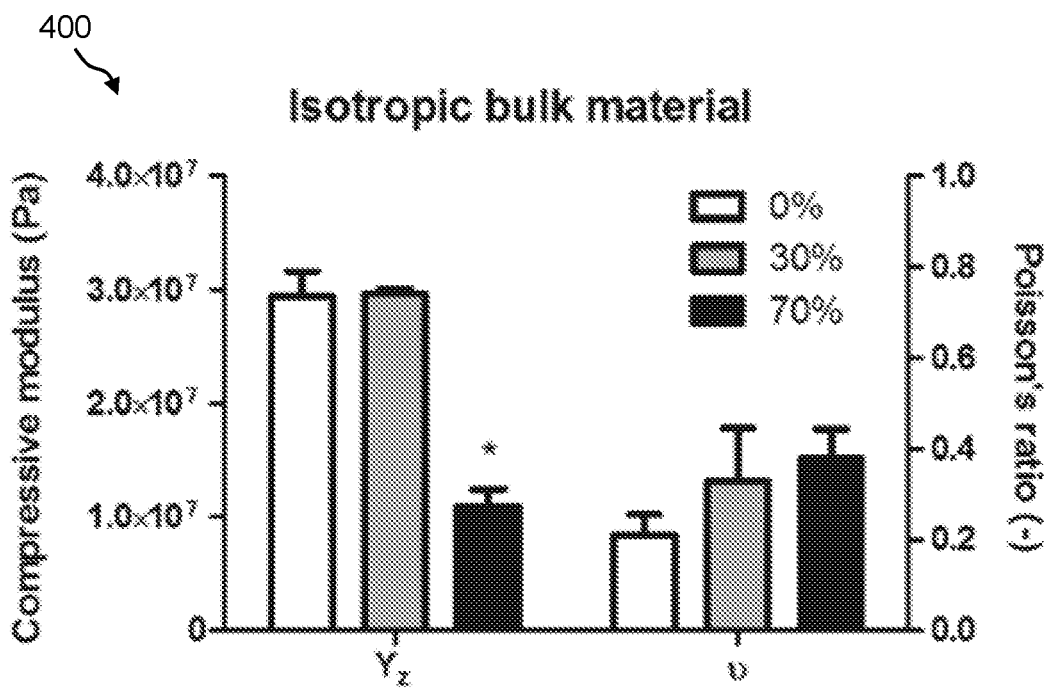
Figure 4B:
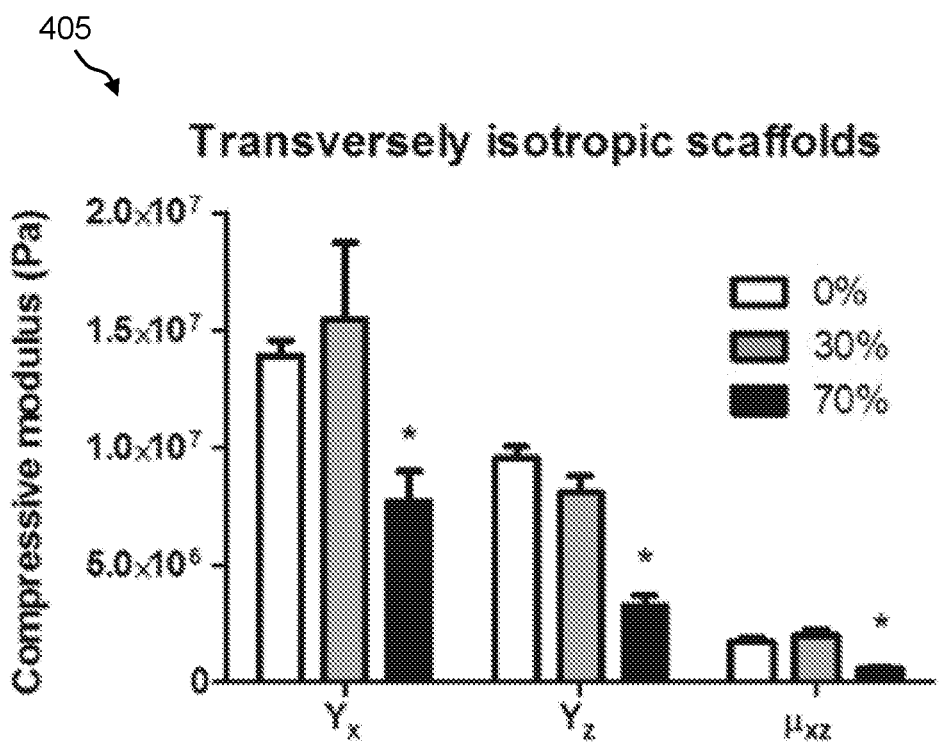
Figure 5A:
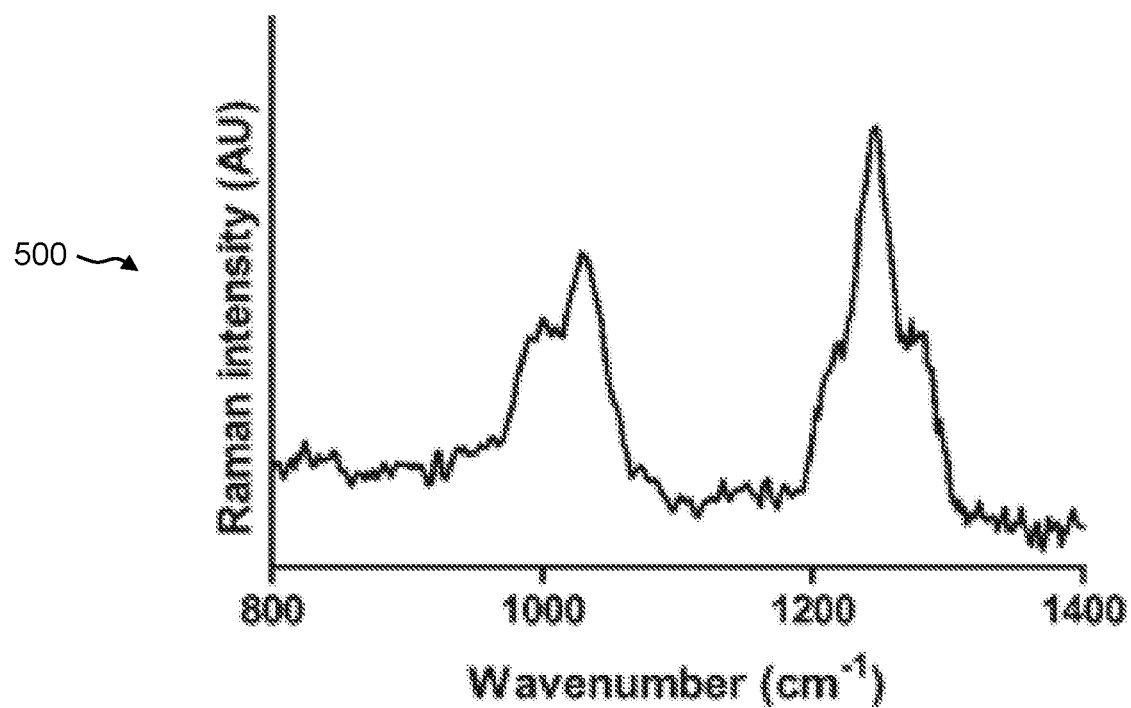
Figure 5B:
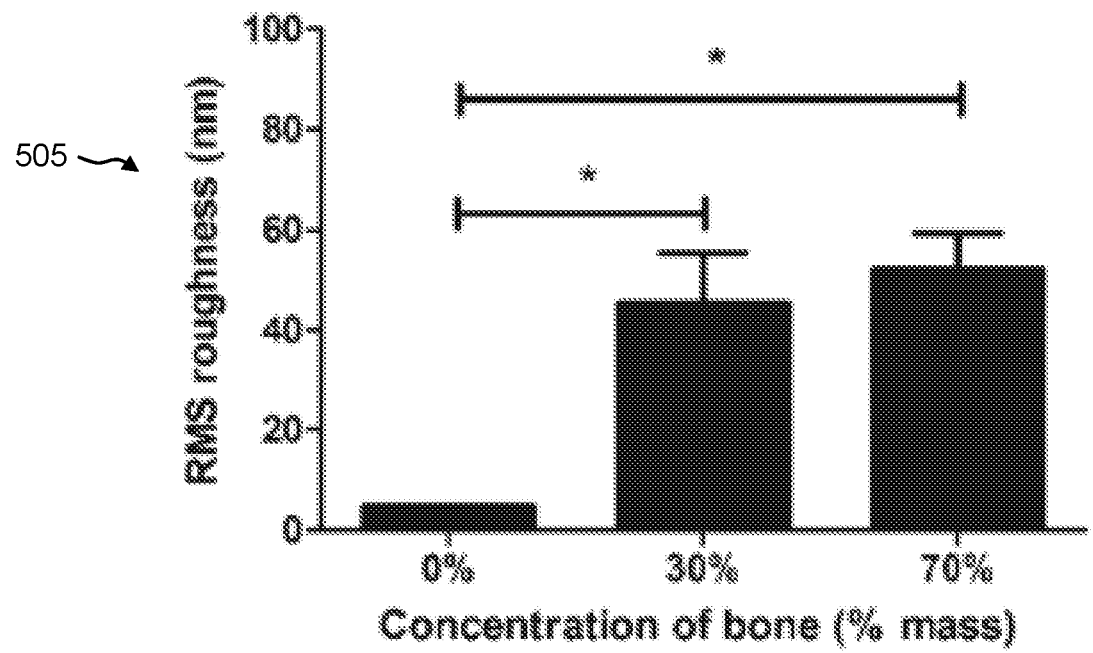
Figure 5C:
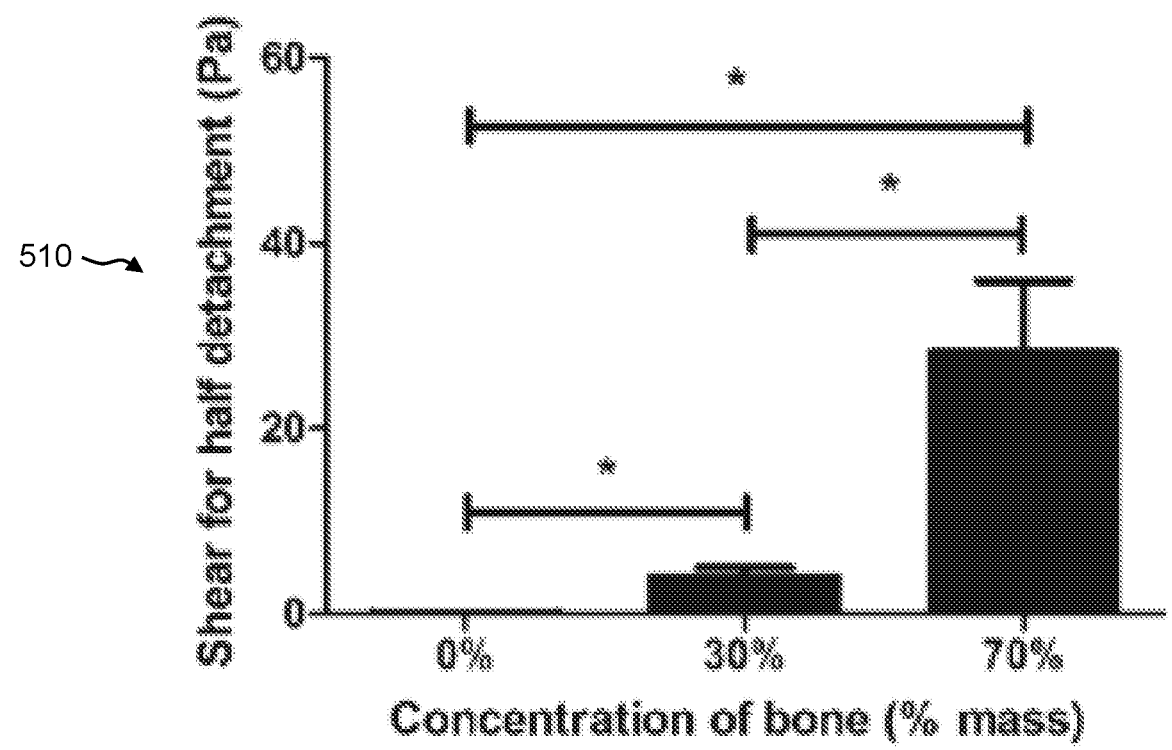
Figure 6A:
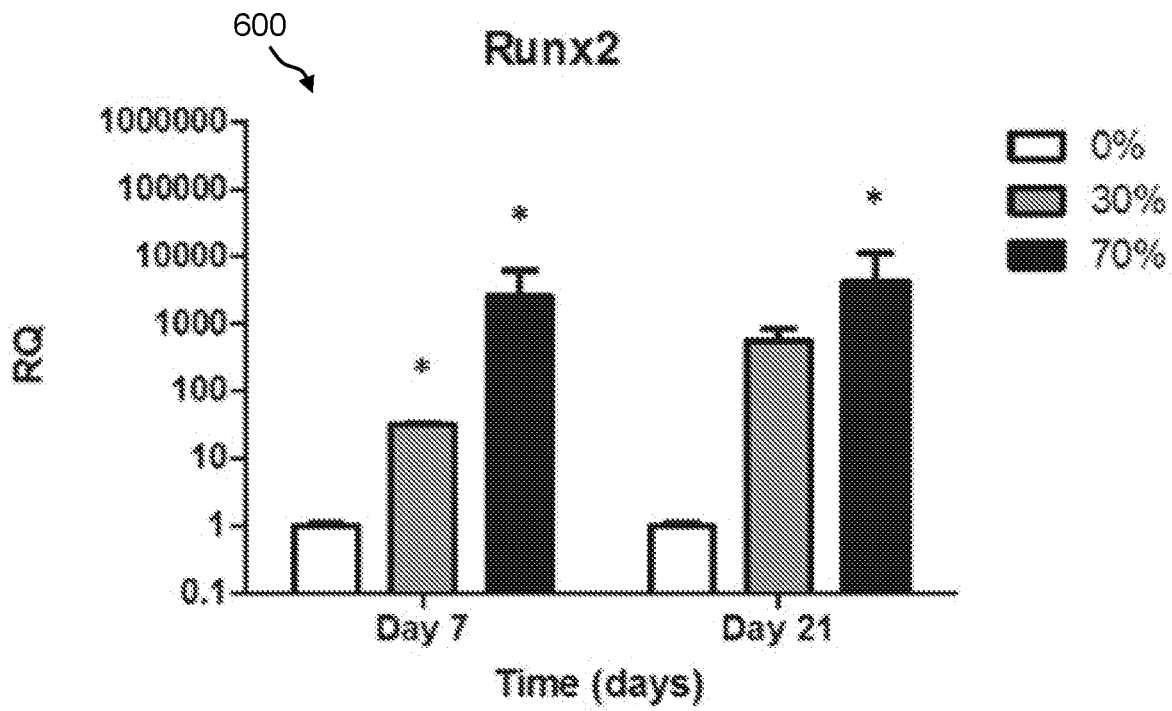
Figure 6B:
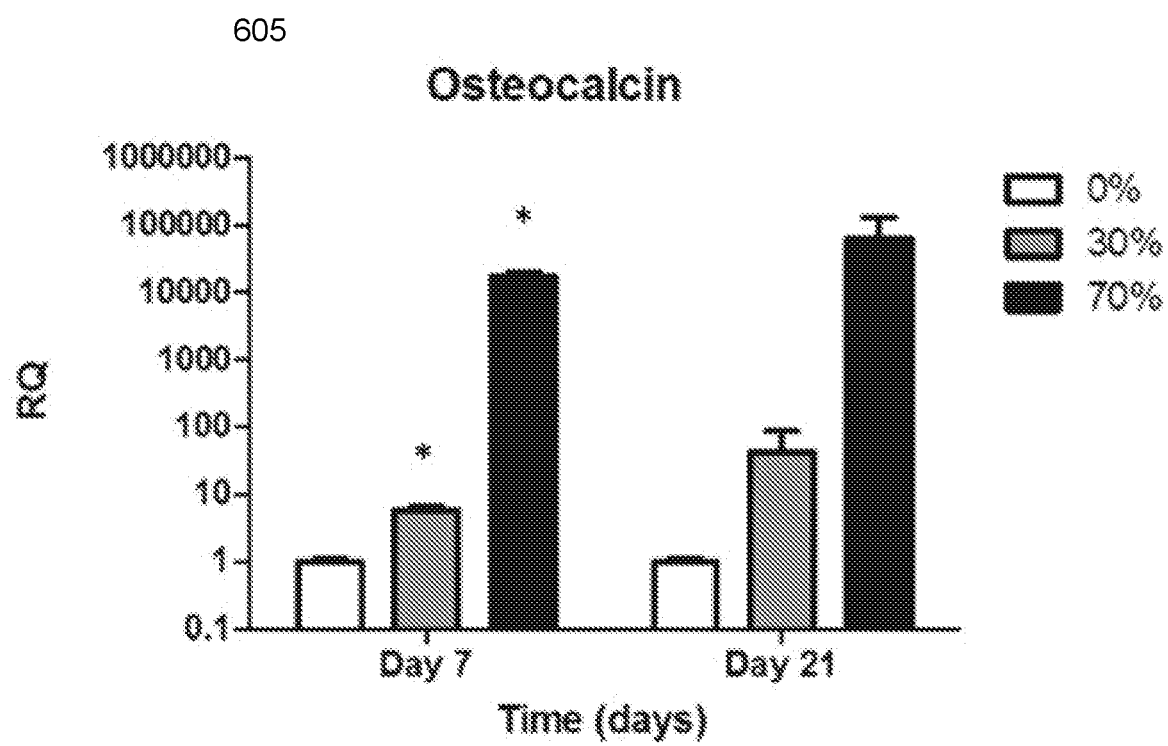
Figure 6C:
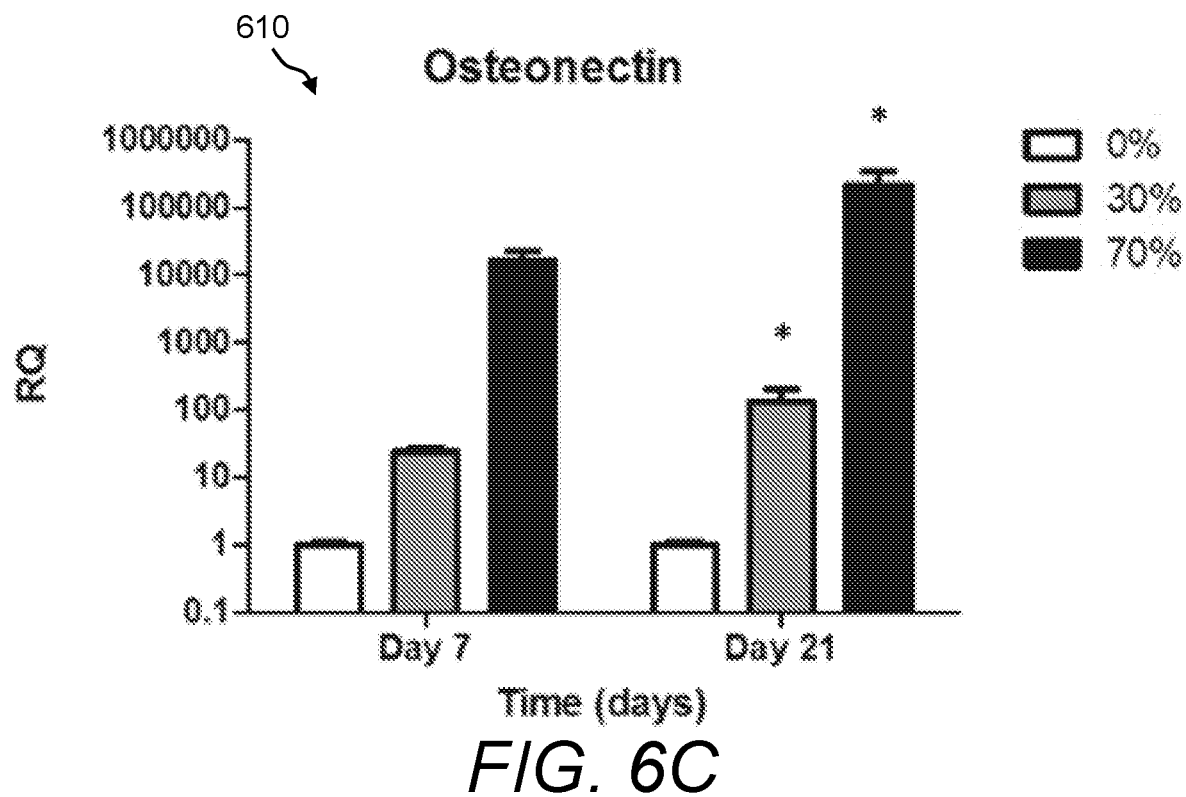
Figure 6D:
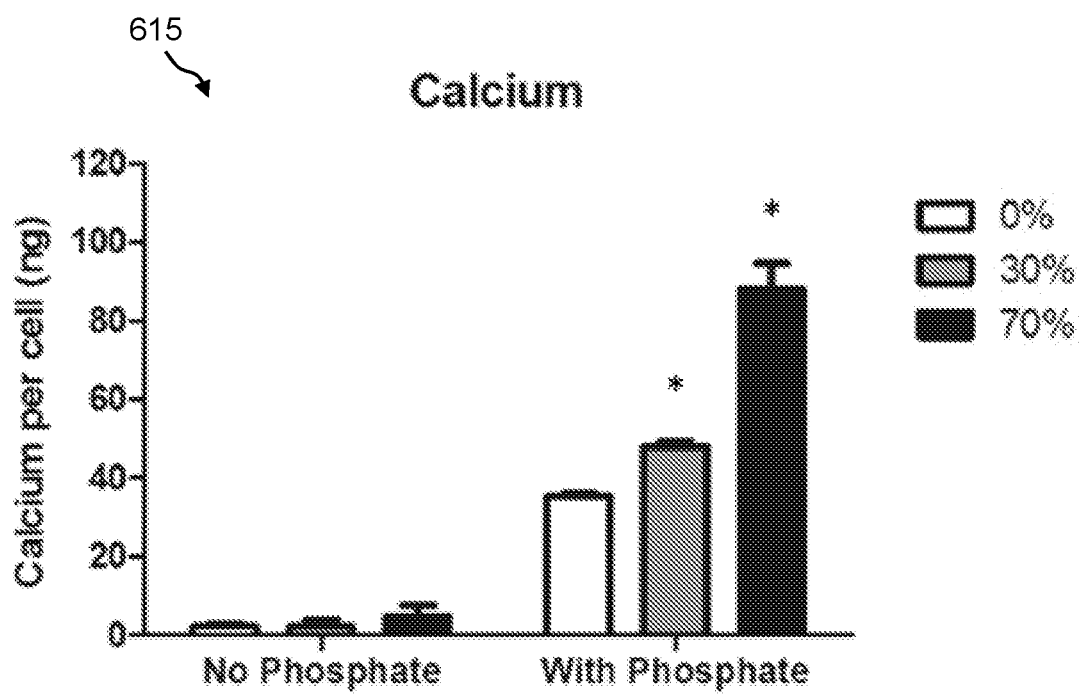
Figure 7:
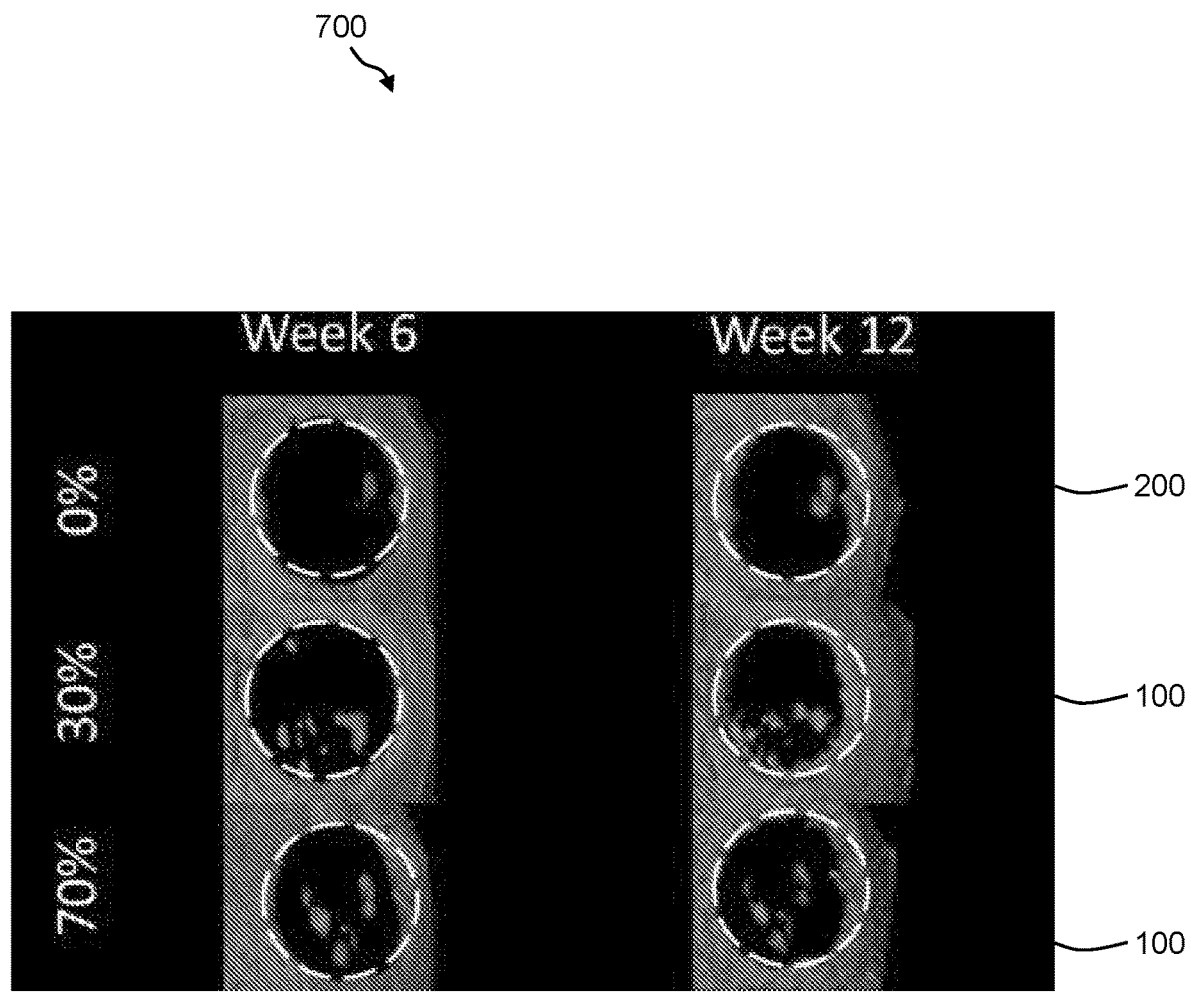
Figure 8:
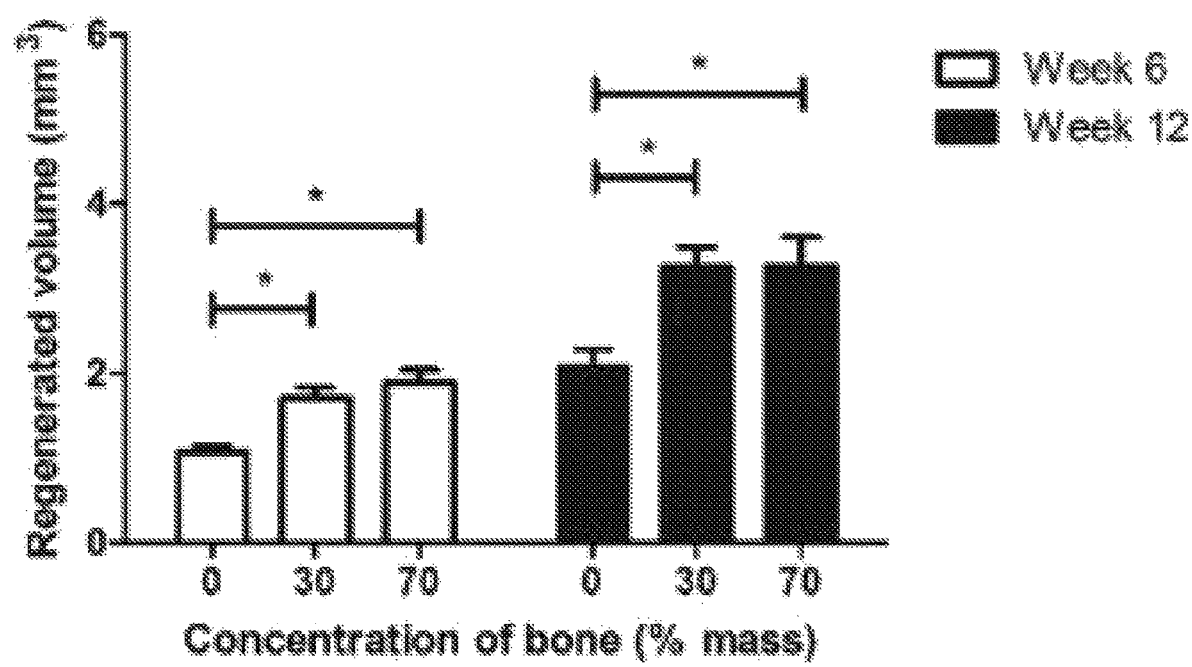
Figure 9:
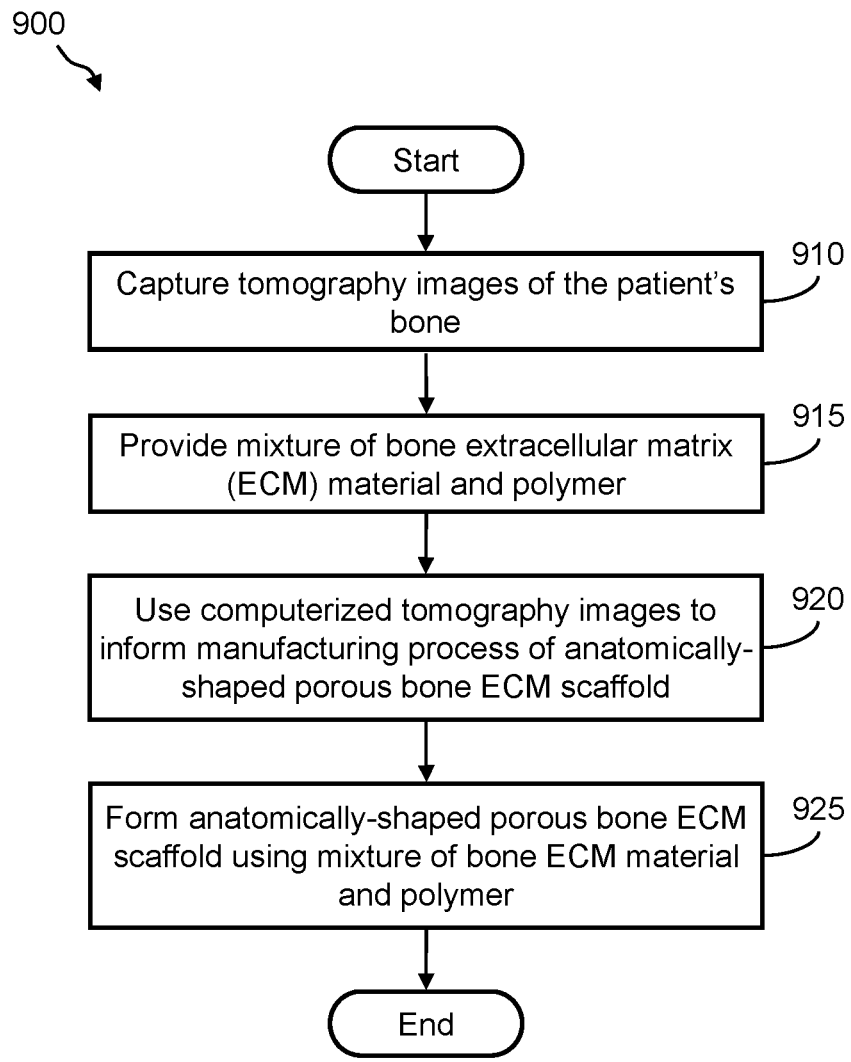
Figure 10:
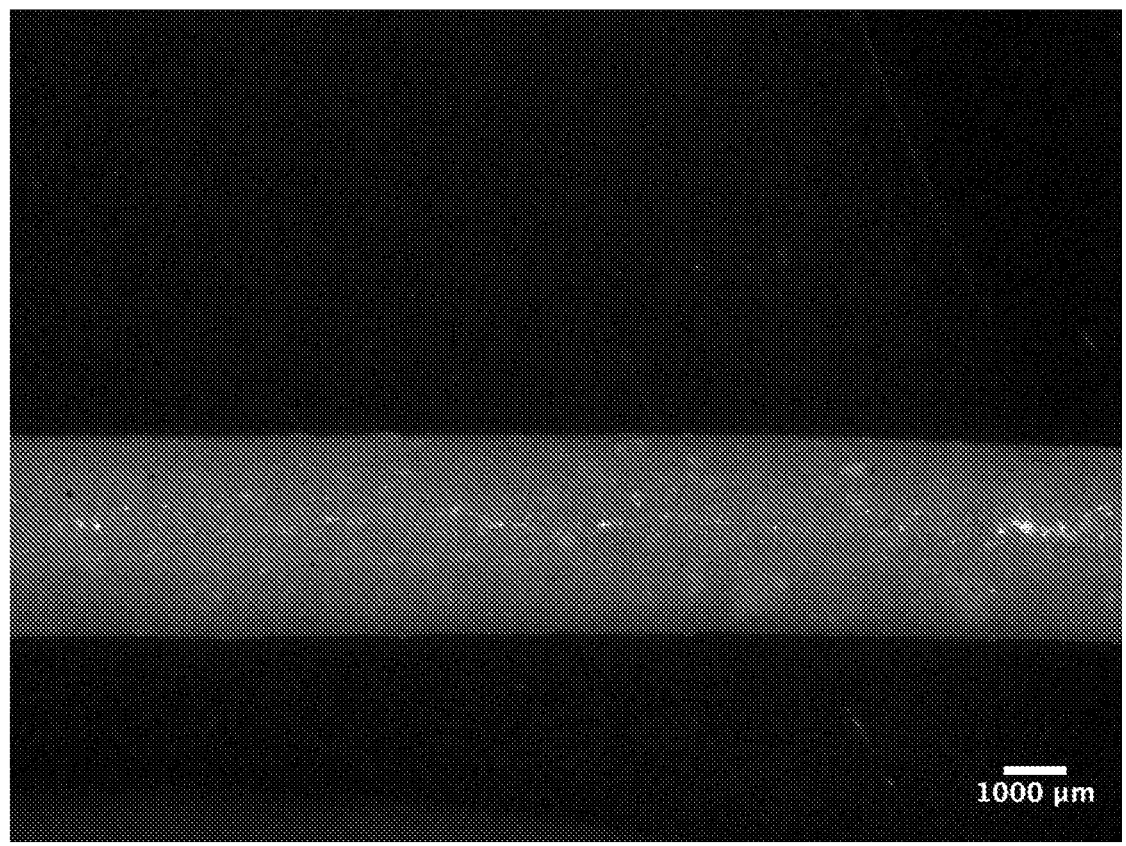
Figure 11:
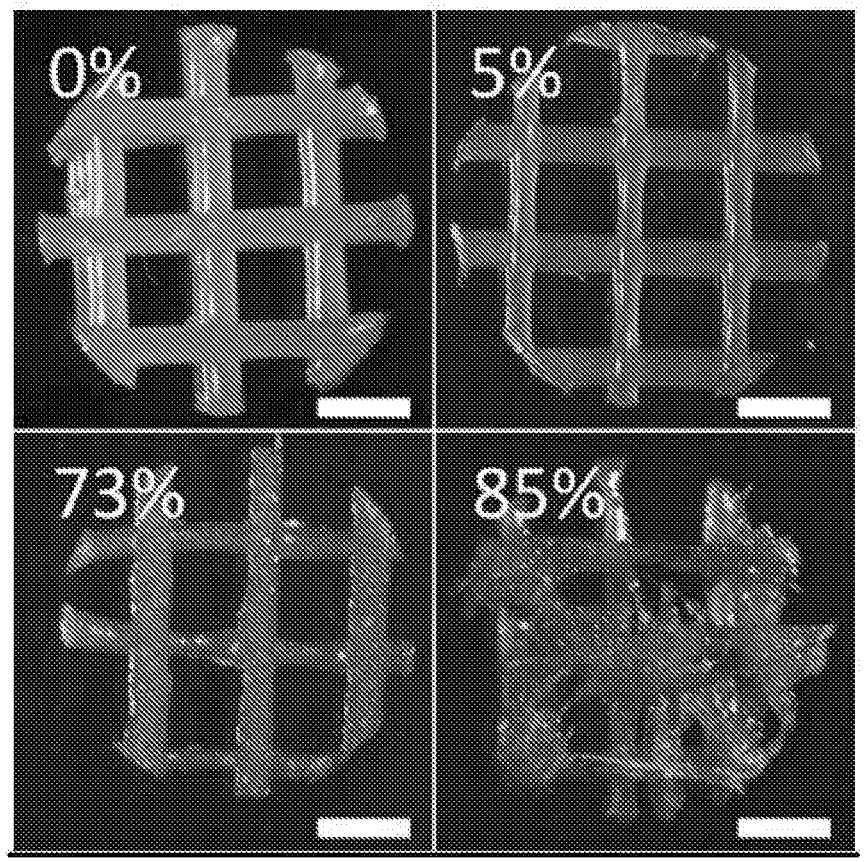
Figure 12:
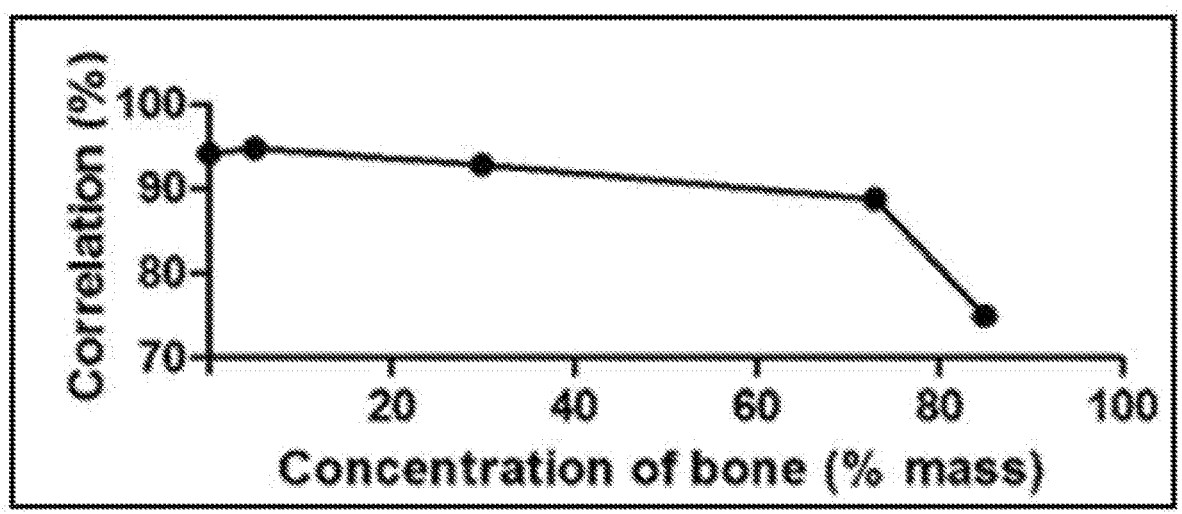
Figure 13:
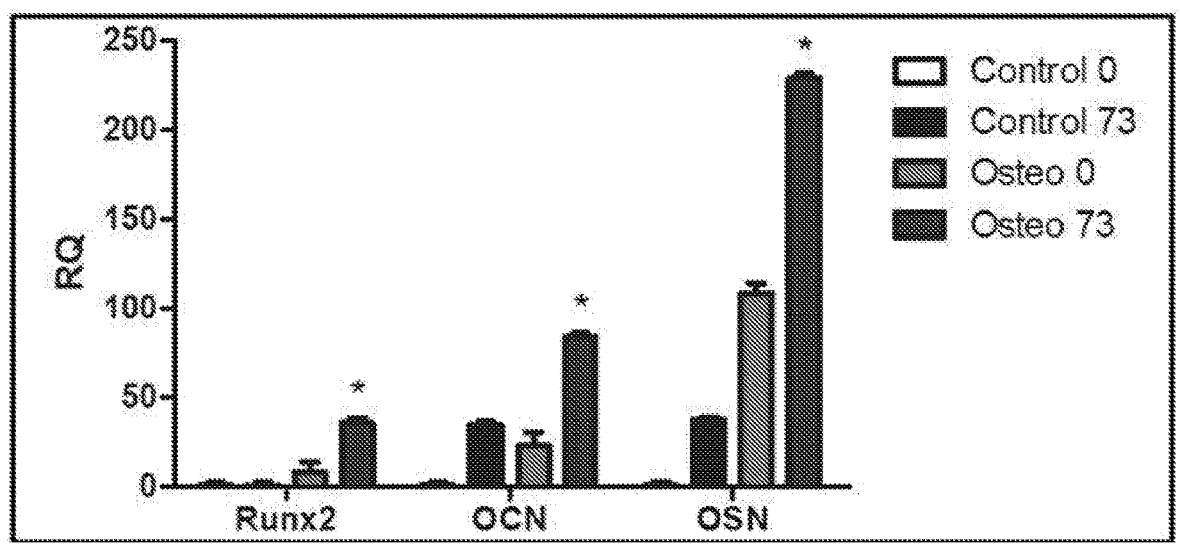
Figure 14:
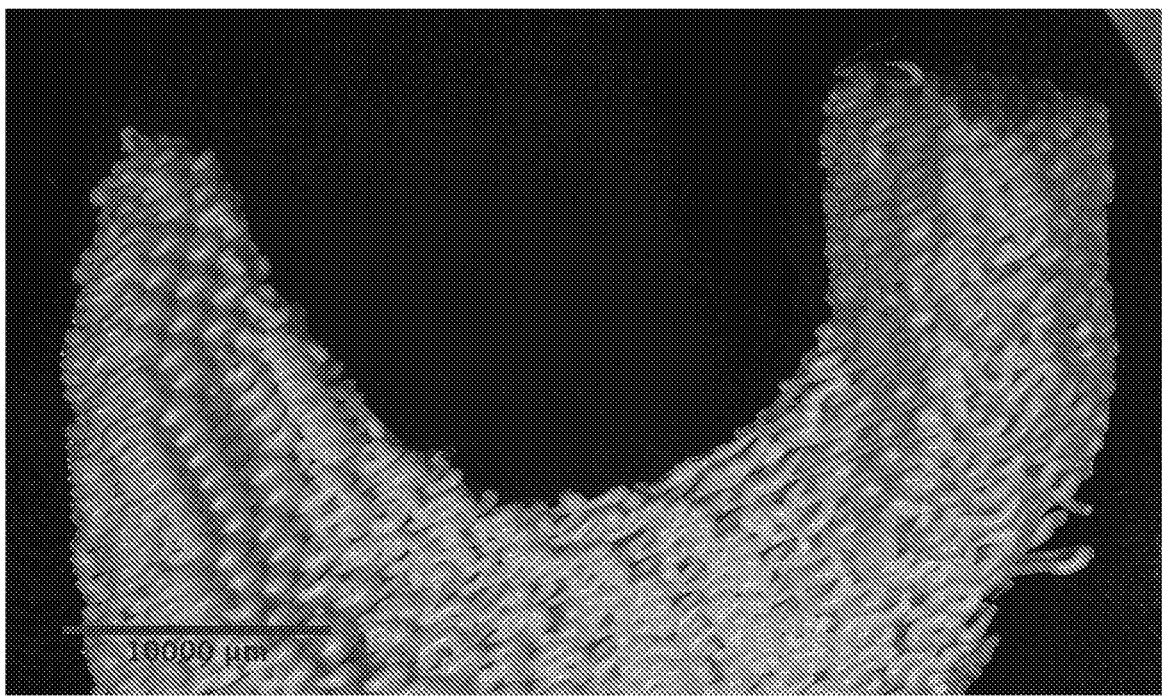
Figure 15:
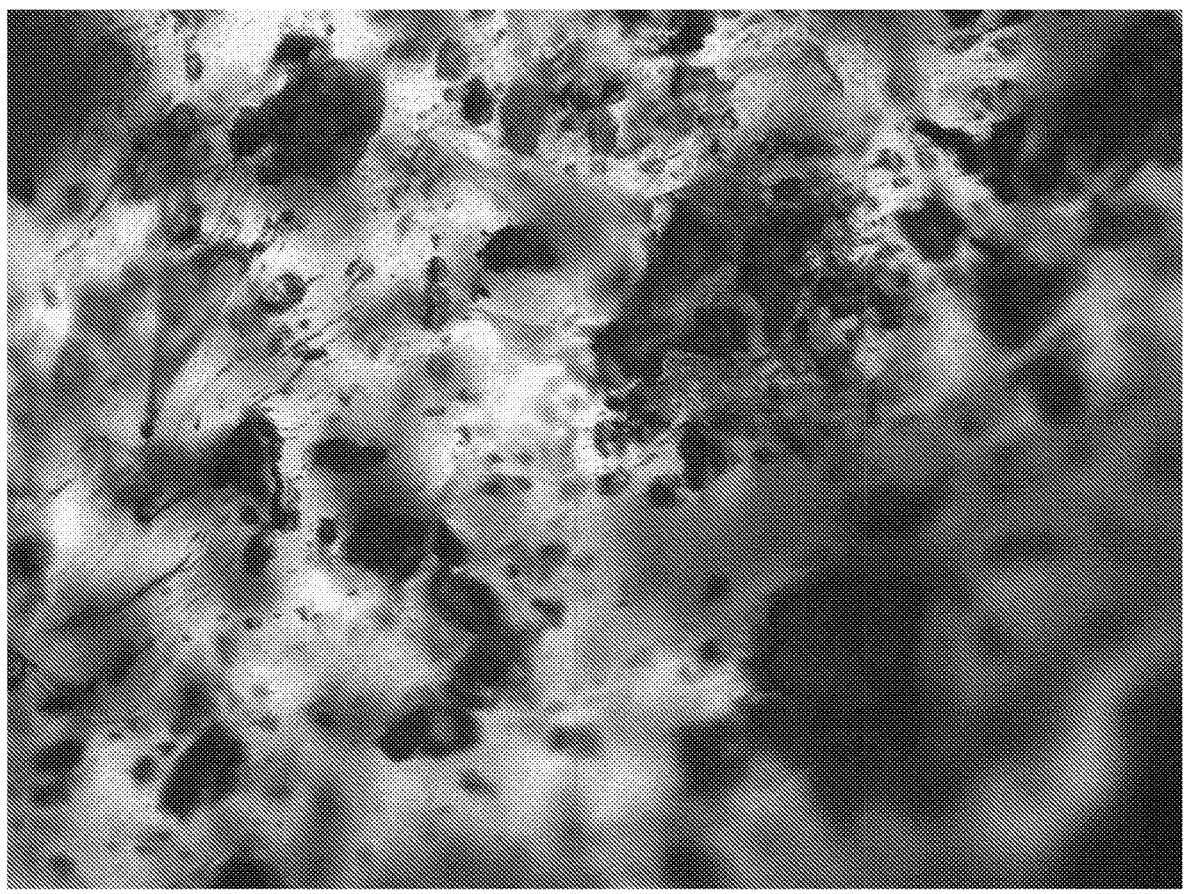
Figure 16A:
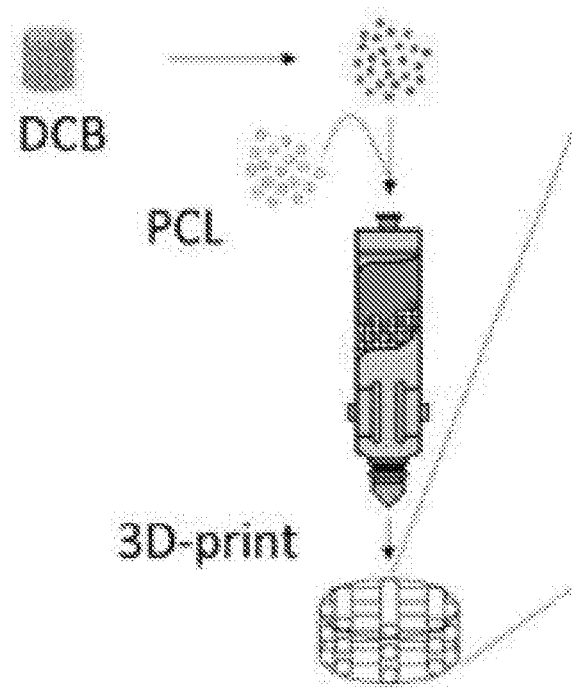
Figure 16B:
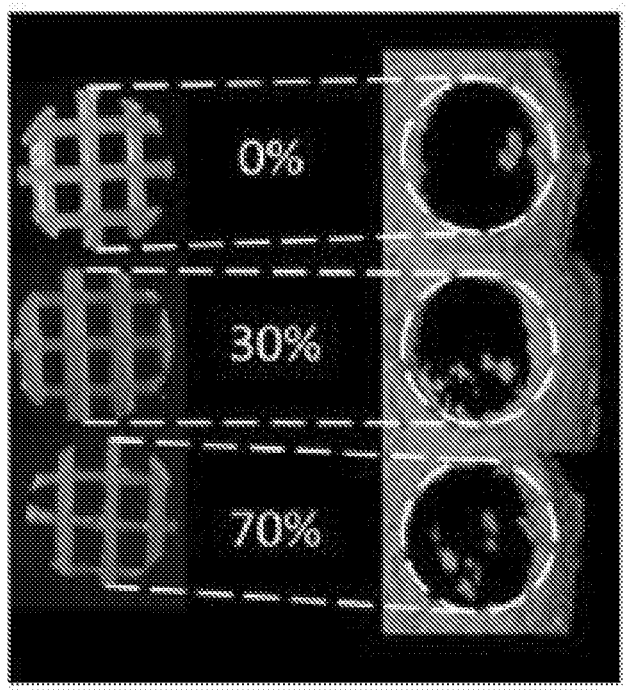
Figure 17:
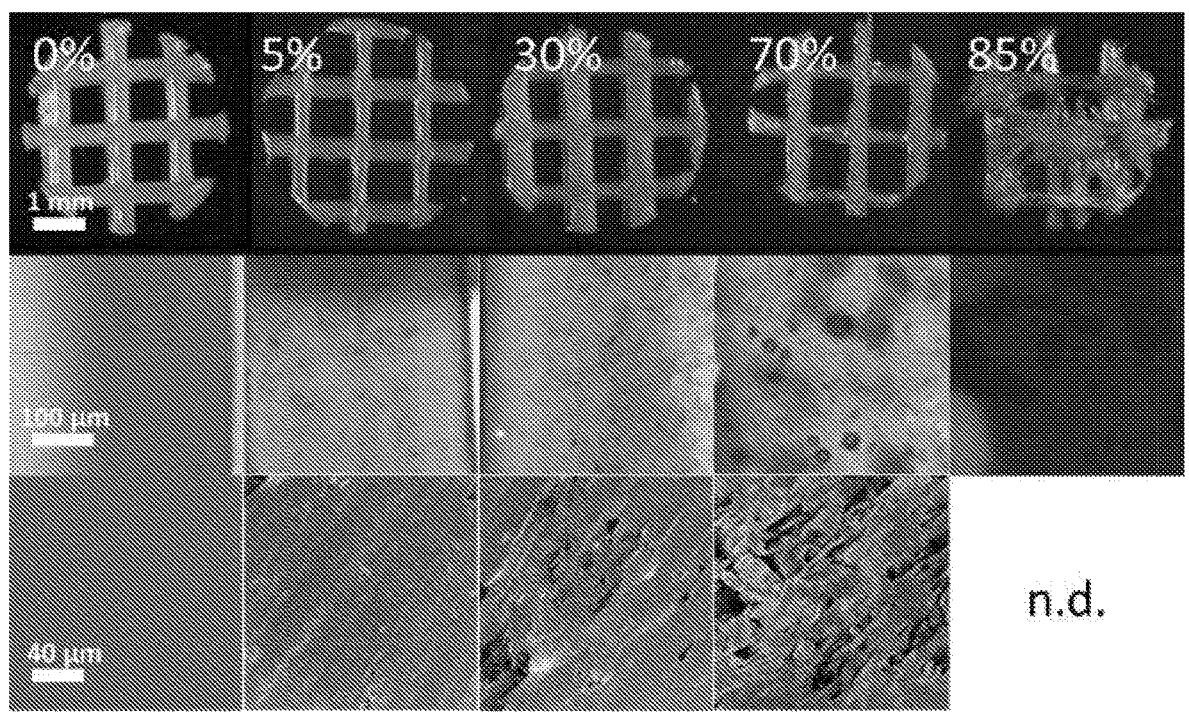
Figure 18A:
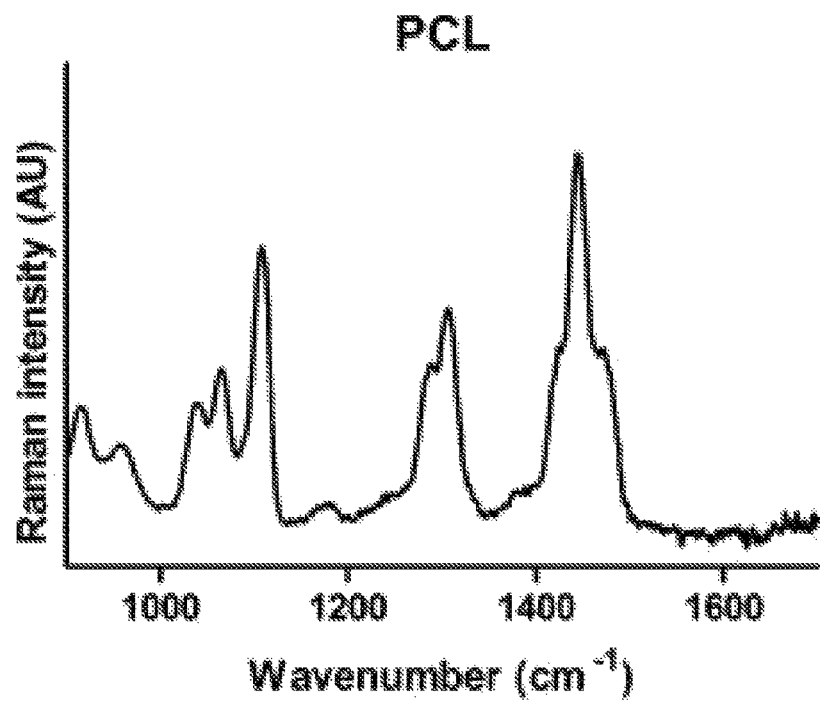
Figure 18B:
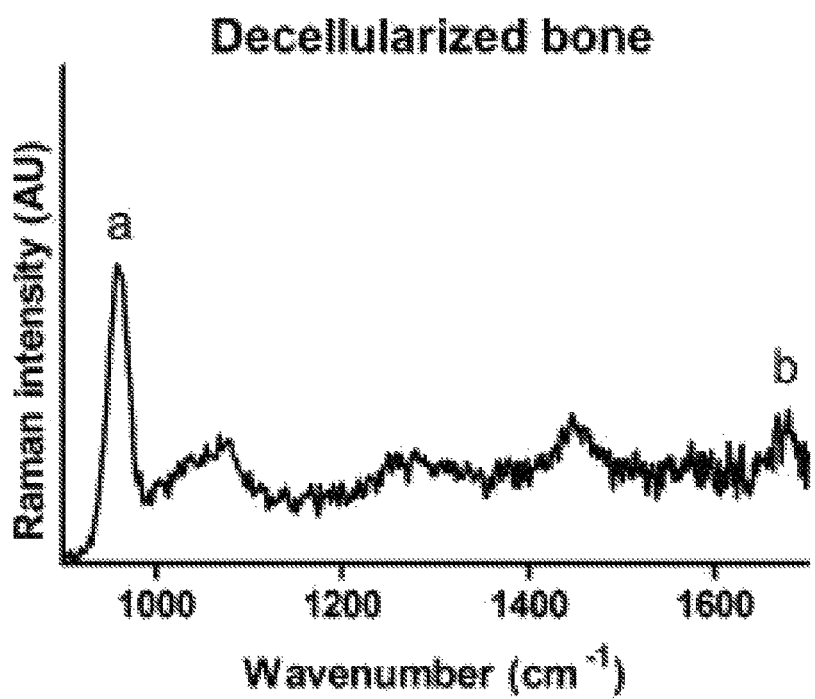
Figure 18C:
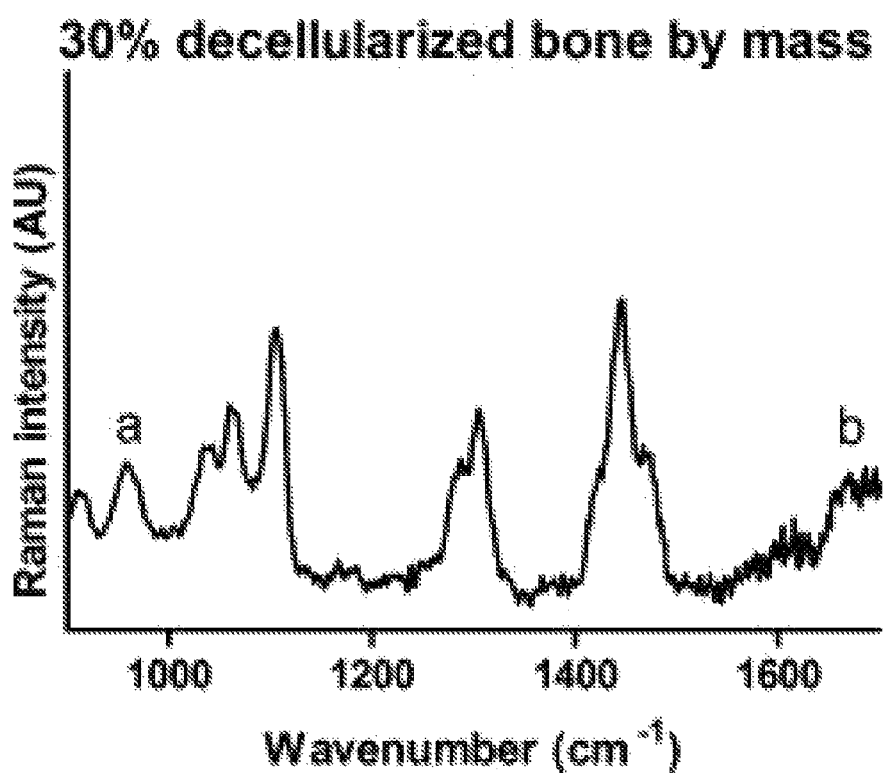
Figure 19A:
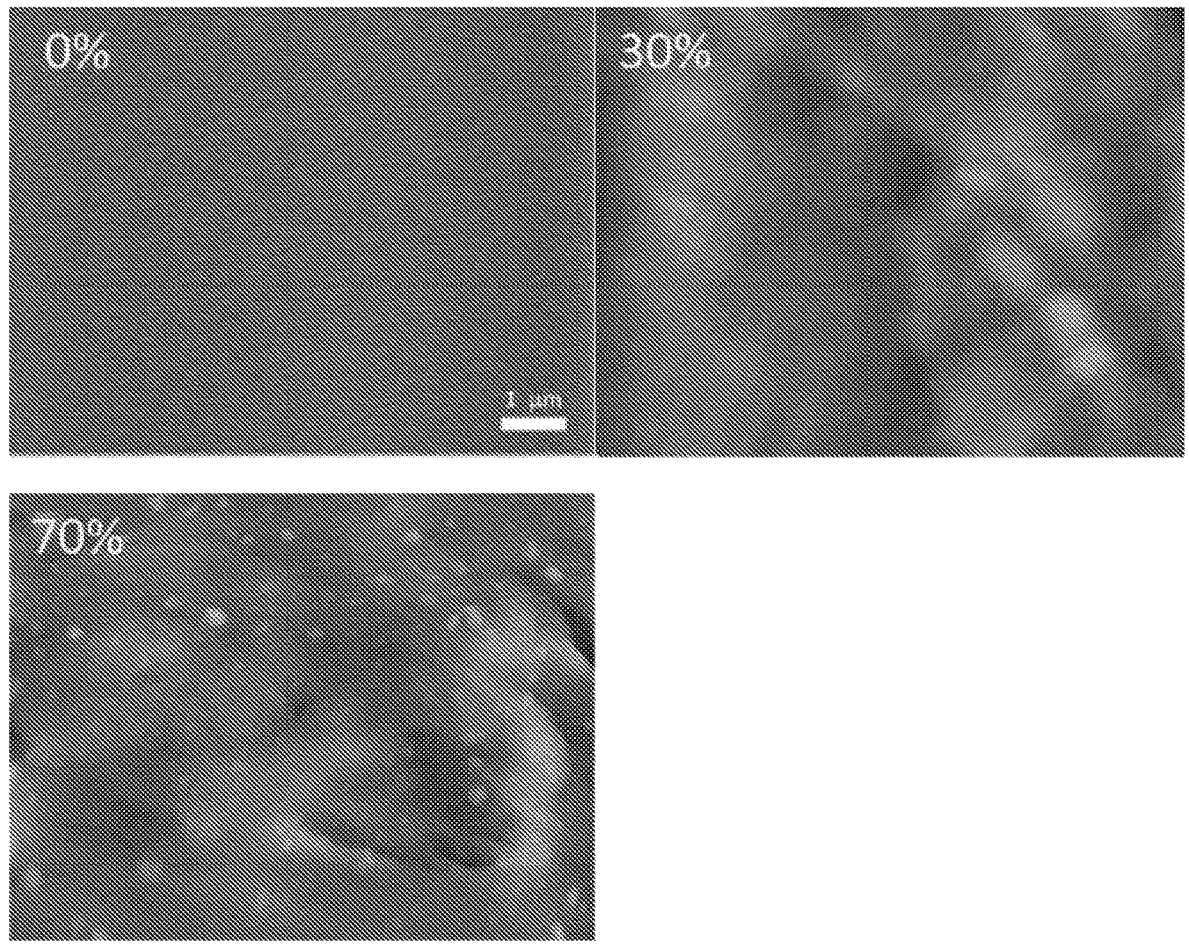
Figure 19B:
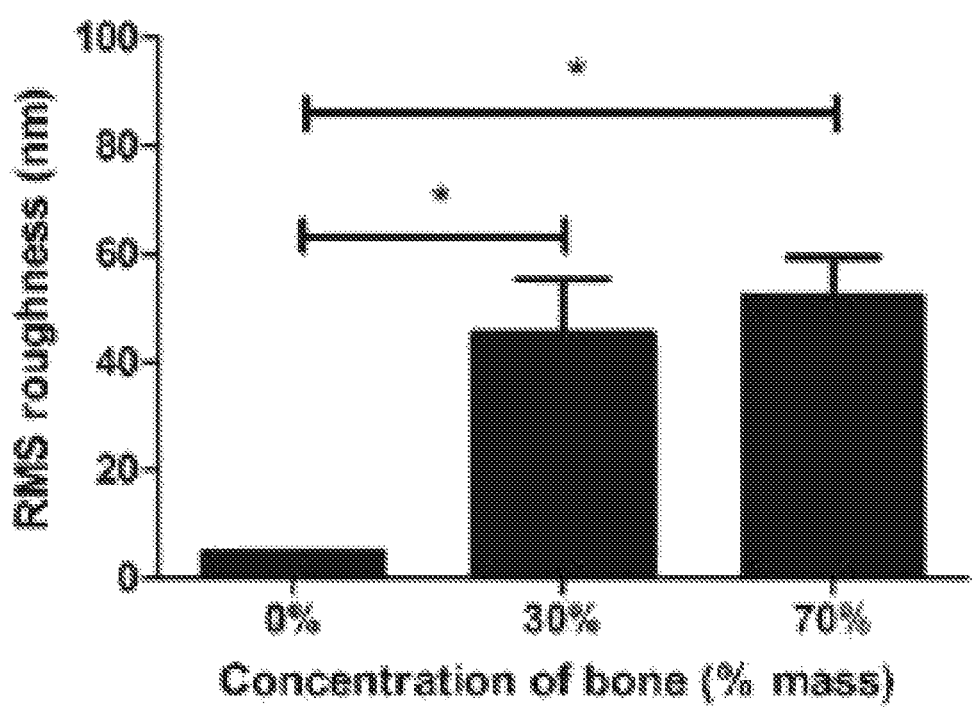
Figure 20A:
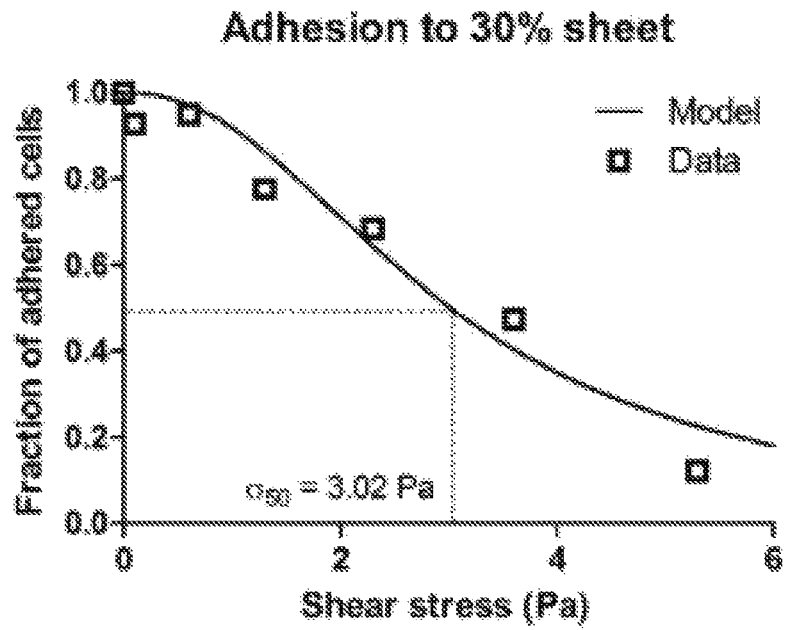
Figure 20B:
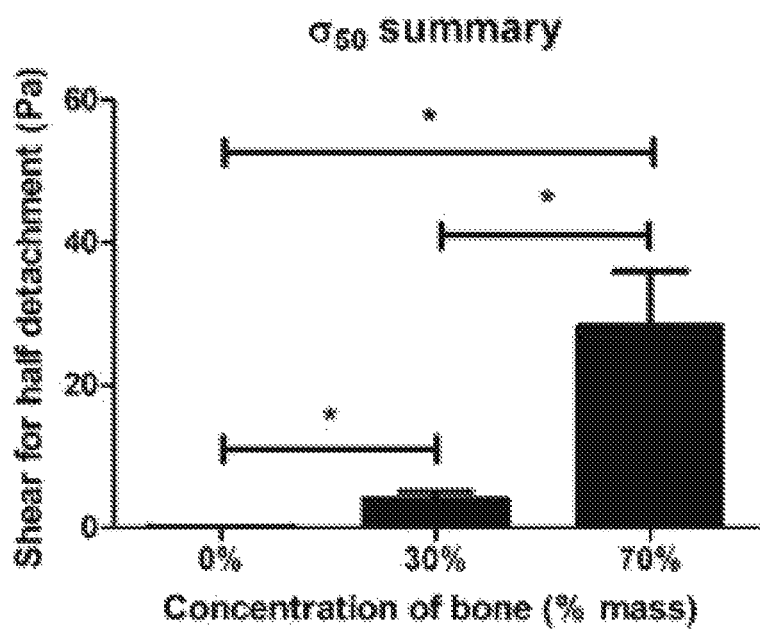
Figure 21:
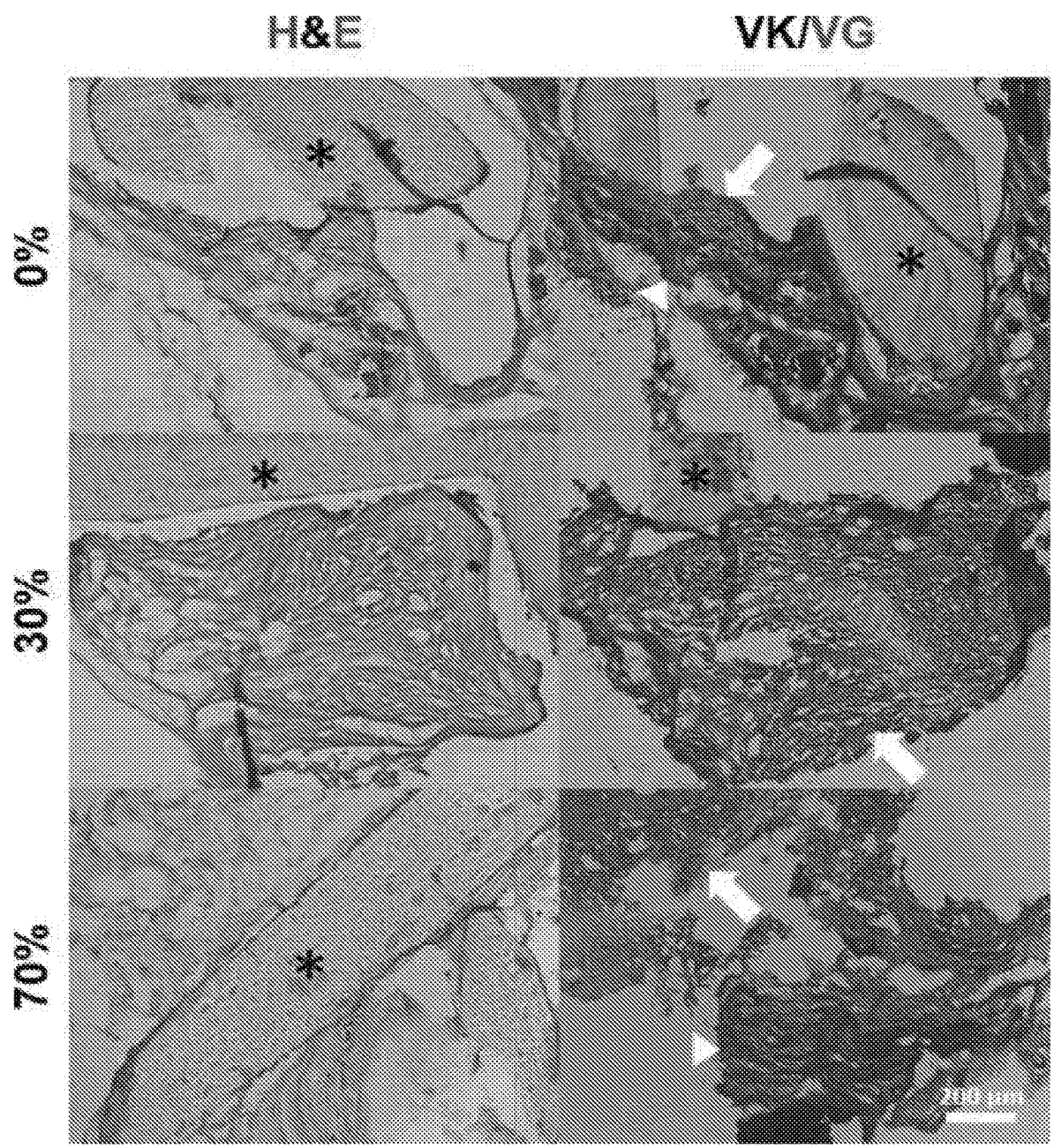
Figure 22:
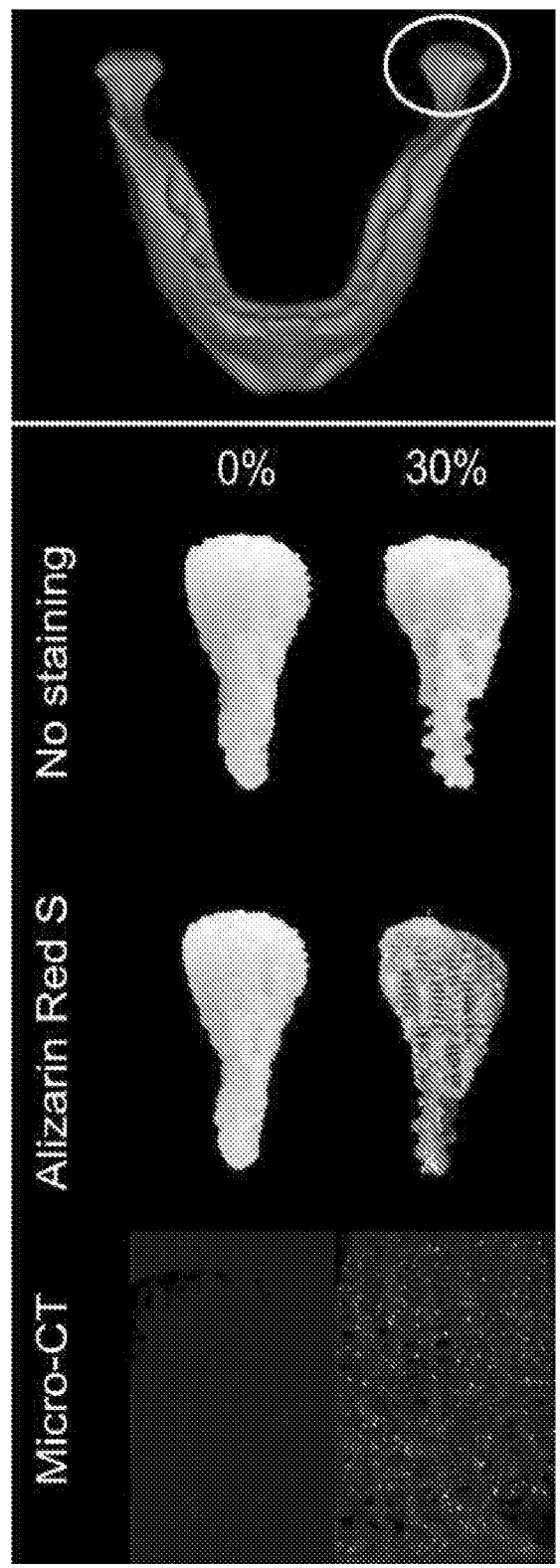
Figure 23:
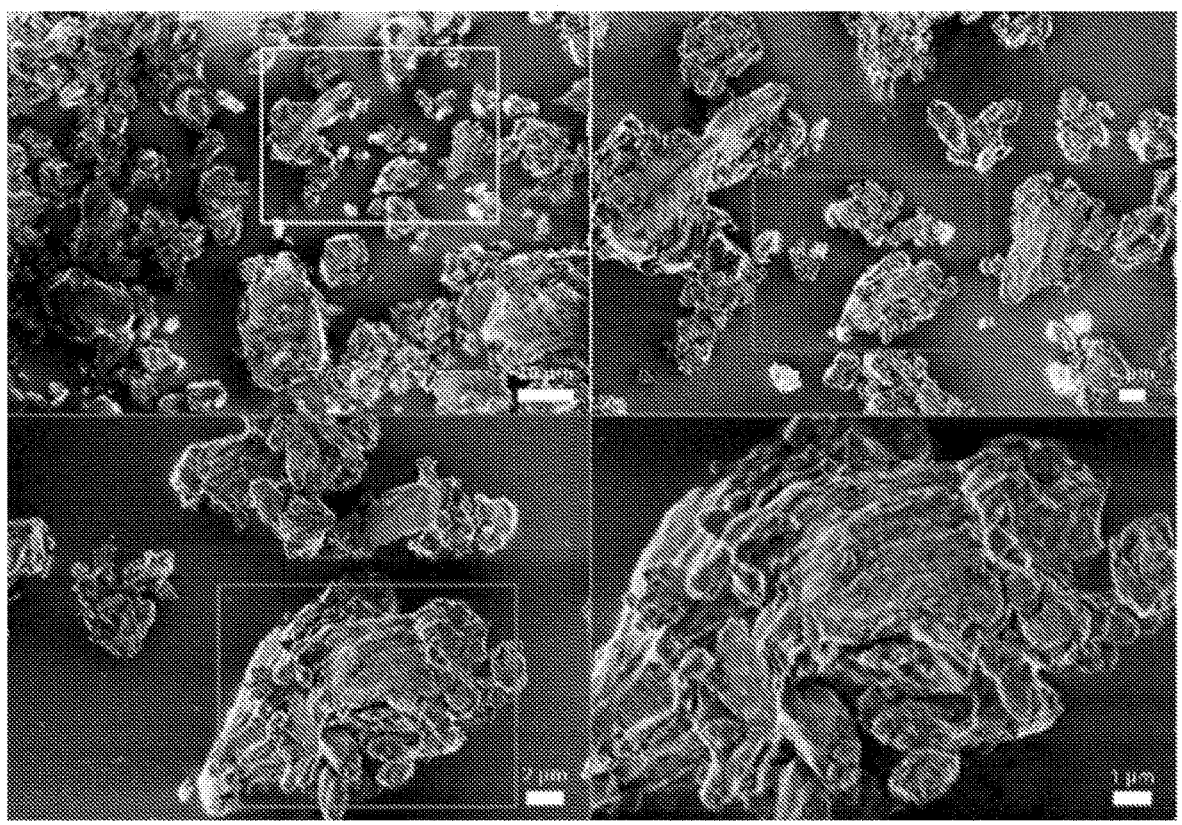
Figure 24:
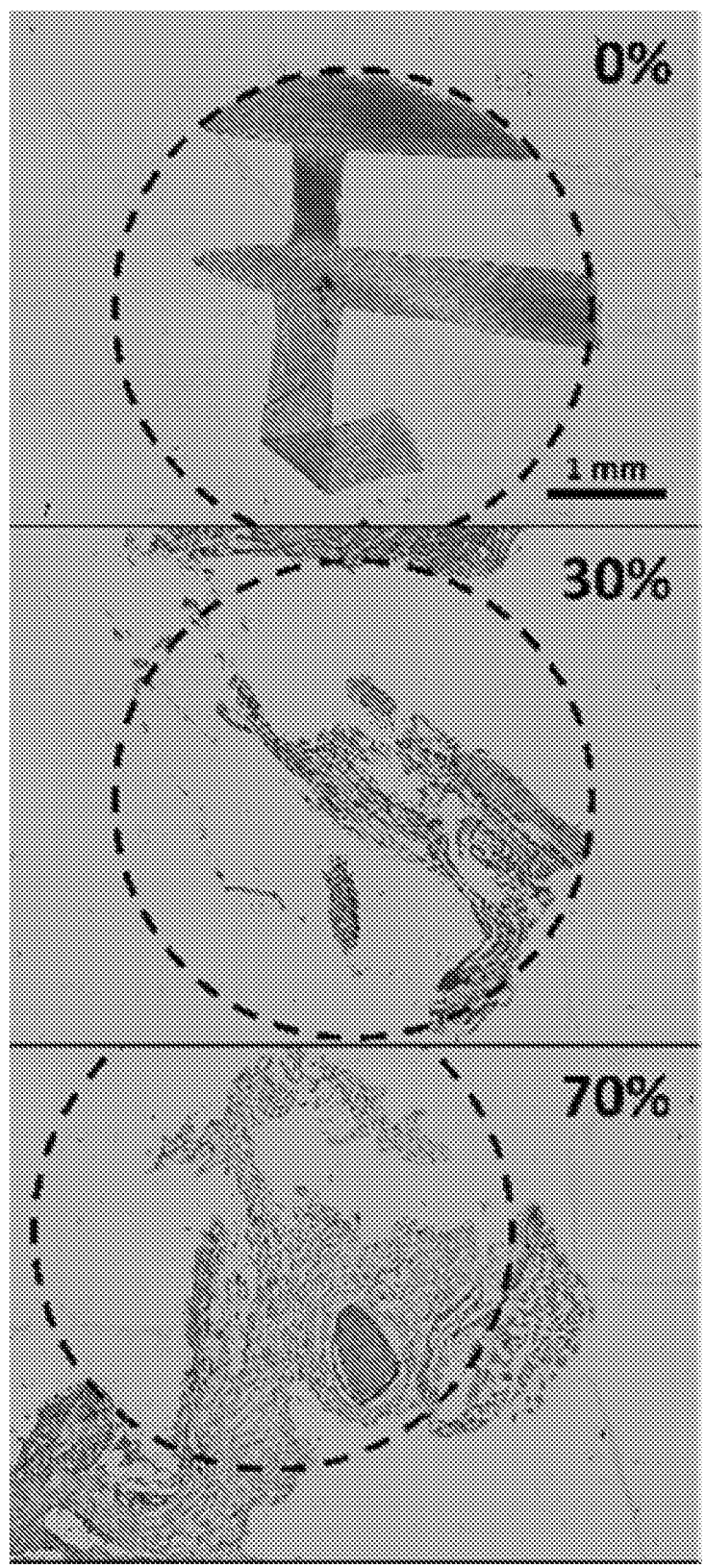

Having thus described the presently disclosed subject matter in general terms, reference will now be made to the accompanying Drawings, which are not necessarily drawn to scale, and wherein:

FIG. 1A is a plan view of an example of a 3D-printed hybrid ECM/PCL scaffold comprising about 5% bone extracellular matrix (ECM);

FIG. 1B is a plan view of an example of a 3D-printed hybrid ECM/PCL scaffold comprising about 30% bone ECM;

FIG. 1C is a plan view of an example of a 3D-printed hybrid ECM/PCL scaffold comprising about 70% bone ECM;

FIG. 1D is a plan view of an example of a 3D-printed hybrid ECM/PCL scaffold comprising about 85% bone ECM;

FIG. 2 is a plan view of an example of a standard 3D-printed scaffold formed without bone ECM material (prior art);

FIG. 3 shows a plot of the print quality of the presently disclosed 3D-printed hybrid ECM/PCL scaffolds as compared to a standard 3D-printed scaffold;

FIG. 4A and FIG. 4B are bar graphs indicating the Mechanical testing of pure and hybrid material/scaffolds of the presently disclosed 3D-printed hybrid ECM/PCL scaffolds. FIG. 4A shows the Poisson's ratios of all groups were not significantly different from each other, whereas the compressive modulus was significantly lower in the 70% group compared to that in both the 30% and pure groups. FIG. 4B shows The same trend held for all directions in transversely isotropic porous scaffolds. *$p<0.05$ compared to pure polycaprolactone by one-way ANOVA with posthoc Tukey test;

FIG. 5A, FIG. 5B, and FIG. 5C are plot and bar graphs indicating the cell adhesion characteristics of the presently disclosed 3D-printed hybrid ECM/PCL scaffolds;

FIG. 6A, FIG. 6B, FIG. 6C, and FIG. 6D are bar graphs with respect to in vitro osteogenic gene expression of the presently disclosed 3D-printed hybrid ECM/PCL scaffolds. Gene expression of Runx2, osteocalcin, and osteonectin increased in cells cultured in hybrid scaffolds despite the absence of exogenous osteoinductive factors. FIG. 6D: With the addition of a phosphate source, calcium production per cell displayed the same trend. *$p<0.05$ compared to cells cultured in pure polycaprolactone scaffolds by one-way ANOVA with posthoc Tukey test;

FIG. 7 shows in vivo regeneration of murine calvarial defect. White dotted lines show boundaries of the original defect. Computed tomography scans at 6 and 12 weeks revealed increased bone regeneration in hybrid ECM/PCL scaffold groups compared to that in the pure polycaprolactone group;

FIG. 8 is a bar graph of quantification of computed tomography scans showing a significant difference between hybrid and pure PCL groups, but no significant difference between the 30% and 70% hybrid ECM/PCL groups shown in FIG. 7;

FIG. 9 illustrates a flow diagram of an example of a method of making the presently disclosed hybrid ECM/polymer scaffolds;

FIG. 10 is a photograph of a filament comprising 30% bone ECM having a diameter of 3 mm. This filament is representative of ECM material that would be fed into a conventional bench or desktop 3D printer to form an anatomical bone or organ;

FIG. 11 is images of (top left) 0%; (top right) 5%; (bottom left) 73%; and (bottom right) 85% bone by mass stained with Alizarin Red S to confirm bone content. Staining visibly increased with increasing bone concentration and is negative for pure PCL (0%). Scalebar: 1 mm;

FIG. 12 is a graph showing that printability was quantified by comparing binary microscope images of printed lattices to a computer-generated perfect lattice. The percentage of matching pixels is termed "correlation factor." Printability steadily declined with increasing bone content and markedly dropped after 73% bone concentration;

FIG. 13 shows RT-PCR of constructs cultured under control or osteogenic conditions for one week revealed an osteoinductive effect of 73% bone scaffolds, with expression of Runx2, osteocalcin (OCN), and osteonectin (OSN) significantly higher than in cells cultured in pure PCL scaffolds. *p<0.05;

FIG. 14 is a photograph of a mandible joint, which is representative of an anatomical shape printed using filament comprising the presently disclosed ECM;

FIG. 15 is a cross section of a filament comprising 30% ECM, wherein the mineral has been stained red, e.g., Alizarin Red stain for calcium;

FIG. 16A is a schematic of a representative 3D printing process for preparing the presently disclosed 3D-printed hybrid ECM/polymer scaffolds;

FIG. 16B shows images of the presently disclosed hybrid ECM/PCL scaffolds comprising 0% ECM, 30% ECM and 70% ECM resulting in the in vivo regeneration of murine calvarial defect as also is shown in FIG. 7. White dotted lines show boundaries of the original defect. Computed tomography scans at 12 weeks revealed increased bone regeneration in hybrid ECM/PCL scaffold groups (30% and 70%) compared to that in the pure polycaprolactone group (0%);

FIG. 17 shows imaging of 3D-printed hybrid scaffolds. Top: Scaffolds stained positively for Alizarin Red S in all cases except for the pure polycaprolactone case. Middle: Magnified images of stained scaffold struts delineating the punctate stain of the mineralized particles within the PCL. Bottom: Scanning electron microscopy of strut surfaces revealing rougher surface topographies in the more concentrated hybrid scaffolds;

FIG. 18A, FIG. 18B, and FIG. 18C show Raman spectroscopy of pure and hybrid materials. Raman spectra of pure polycaprolactone, revealing peaks at 1450 cm$^{-1}$ for δCH2, 1300 cm$^{-1}$ for ωCH2, and 1110 cm$^{-1}$ for skeletal stretching (FIG. 18A); Raman spectra of decellularized trabecular bone, showing peaks at 960 cm$^{-1}$ for phosphate (a) and 1650 cm$^{-1}$ for collagen amide I (b) (FIG. 18B); and Raman spectra of 30% DCB:PCL (FIG. 18C). The bone only peaks, as well as the peaks corresponding to contributions from both bone and polycaprolactone appear;

FIG. 19A shows atomic force microscopy of pure and hybrid materials. Top left: Atomic force micrograph of pure polycaprolactone (0% bone by mass) is mostly featureless, whereas surface features are rougher for 30% bone by mass (top right) and 70% bone by mass (bottom left);

FIG. 19B shows quantification of root-mean-square roughness confirming the observations from FIG. 19A. *p<0.05 by one-way ANOVA with posthoc Tukey test;

FIG. 20A and FIG. 20B show cell adhesion to pure and hybrid materials. FIG. 20A is a representative graph of adhered cells plotted against shear with a variable-slope concentration response model fit to determine the shear for half-detachment, σ50. FIG. 20B show that σ50 increases in a dose-dependent manner with increasing bone concentration. *p<0.05 by one-way ANOVA with posthoc Tukey test;

FIG. 21 shows histological analysis of excised constructs. Cellularity under hematoxylin and eosin staining (left), as well as bone (black/dark brown) and osteoid (red) formation under the von Kossa and van Gieson stains (right) is evident. Asterisks denote scaffold struts. In the von Kossa and van Gieson stains, note the presence of both osteoid (red, arrowheads) and mineralized tissue (red/brown, arrows), suggesting active mineralization occurring within the constructs;

FIG. 22 shows (Top): Anatomical shape printing of pure and hybrid scaffolds. (Middle): A human temporomandibular joint condyle was isolated and printed into anatomically shaped, porous scaffolds. Scaffolds were subject to Alizarin Red S staining to confirm and visualize the presence of mineralized particles in the hybrid scaffold. (Bottom): MicroCT scans performed to confirm the presence of mineralized particles in the 30% DCB:PCL scaffolds. There were no mineral particles in the pure PCL scaffold;

FIG. 23 shows scanning electron microscopy of cryo-milled bone particles that had been run through a 40-μm filter. Sizes of particles above 40 μm are absent. Boxes show images of increased magnification; and FIG. 24 shows in vivo host cell infiltration into pure and hybrid scaffolds one week post-implantation. Black dotted lines show boundaries of scaffolds while the haematoxylin/eosin stain shows infiltration of host cells. Infiltration is negligible in the pure scaffolds and increases with increasing concentration of bone in the hybrid scaffolds.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Bone engineering has great potential to solve the current clinical shortage of available donor tissue for transplantation. For bone regeneration, the scaffold, which provides both structural and geometrical guidance, is critical. While naturally-derived scaffolds impart bioactivity via embedded biomolecules, they suffer from long, challenging preparation procedures; batch-to-batch variability; and difficulty in achieving the appropriate gross anatomical geometry. Synthetic, biodegradable, polymeric scaffolds are more easily processed into desired geometries in a highly consistent manner, especially via three-dimensional printing. Synthetic biopolymers, however, are generally bioinert.

In contrast, the presently disclosed subject matter provides a composite scaffold that is produced by cryo-milling decellularized trabecular bone or other source of ECM material, incorporating the resulting particles into a greater biocompatible polymer phase, e.g., a PCL phase, and forming a porous hybrid ECM/polymer scaffold by a 3D printing process. Without wishing to be bound to any one particular theory, it is thought that the embedded bone particles will provide osteoinductivity and osteoconductivity while the biocompatible polymer, e.g., PCL, will allow for 3D-printing-based control over macro- and micro-geometry.

Accordingly, in some embodiments, the presently disclosed subject matter provides an extracellular matrix (ECM) mixture, anatomically-shaped porous ECM scaffolds, and a method of making the anatomically-shaped porous ECM scaffolds using the ECM mixture.

As provided herein, the presently disclosed extracellular matrix comprises material selected from the group consisting of trabecular bone, also referred to as cancellous bone or spongy bone; cortical bone, also referred to as compact bone; connective tissue, such as cartilage; and combinations thereof. Other sources of extracellular matrix material, such as skeletal muscle, tendons, and ligaments also are contemplated by the presently disclosed subject matter. Further, the material comprising the extracellular matrix can comprise various degrees of mineralization, including, but not limited to, fully mineralized, partially mineralized, demineralized, and combinations thereof.

In some embodiments, the ECM mixture can comprise from about 5% to about 85% by weight of the ECM material and from about 15% to about 95% by weight of a biocompatible polymer material, such as, but not limited to, a biodegradable polyester. Further, the particle size of the ECM material in the ECM mixture can be from about less than 1 micron to about several hundred microns, or in some embodiments, less than 100 microns, such as 40 microns or less. The ECM material is provided in the scaffold to promote bone or organ regeneration. By combining native bone or connective tissue, e.g., cartilage, with a biocompatible polymer material, manufacturability and bioactivity can both be attained using a single approach.

Further, in some embodiments, the presently disclosed scaffold can comprise a gradient of the amount, e.g., percentage, of ECM found throughout the scaffold.

In some embodiments, the presently disclosed anatomically-shaped porous ECM scaffolds can be formed using a three-dimensional (3D) printing process or a so-called additive manufacturing process. In other embodiments, the presently disclosed anatomically-shaped porous ECM scaffolds can be formed using an injection molding process or any other process.

Referring now to FIG. 1A, FIG. 1B, FIG. 1C, and FIG. 1D are examples of the presently disclosed 3D-printed ECM scaffolds 100 formed using the presently disclosed bone ECM mixture. Table 1 shows an example of the contents of the presently disclosed bone ECM mixture for forming the 3D-printed ECM scaffolds 100.

Further, in Table 1, the particle size of the ECM material, e.g., bone ECM material, can be from about less than one micron to about several hundred microns, or in some embodiments less than 40 microns. The presence of the ECM material in the mixture promotes bone or organ regeneration when using the presently disclosed 3D-printed ECM scaffolds 100. Namely, the higher the concentration of ECM material in the 3D-printed ECM scaffolds 100 the better the bone or organ regeneration.

TABLE 1

| Example ECM mixtures | |
|---|---|
| Ingredient | Percent (%) by weight |
| General ECM mixture | |
| ECM material | about 5% to about 85% |
| Polymer material | about 15% to about 95% |
| Specific example #1 | |
| ECM material | about 5% |
| Polymer material | about 95% |
| Specific example #2 | |
| ECM material | about 30% |
| Polymer material | about 70% |
| Specific example #3 | |
| ECM material | about 70% |
| Polymer material | about 30% |
| Specific example #4 | |
| ECM material | about 85% |
| Polymer material | about 15% |

FIG. 1A is a plan view of an example of a 3D-printed ECM scaffold 100 that includes about 5% bone ECM material according to specific example #1 of Table 1. This 3D-printed ECM scaffold 100 is hereafter called the 5%-3D-printed ECM scaffold 100.

FIG. 1B is a plan view of an example of a 3D-printed ECM scaffold 100 that includes about 30% bone ECM material according to specific example #2 of Table 1. This 3D-printed ECM scaffold 100 is hereafter called the 30%-3D-printed ECM scaffold 100.

FIG. 1C is a plan view of an example of a 3D-printed ECM scaffold 100 that includes about 70% bone ECM material according to specific example #3 of Table 1. This 3D-printed ECM scaffold 100 is hereafter called the 70%-3D-printed ECM scaffold 100.

FIG. 1D is a plan view of an example of a 3D-printed ECM scaffold 100 that includes about 85% bone ECM material according to specific example #4 of Table 1. This 3D-printed ECM scaffold 100 is hereafter called the 85%-3D-printed ECM scaffold 100.

FIG. 1A, FIG. 1B, FIG. 1C, and FIG. 1D also show a panel 105 that is a magnified view of the respective struts of the 3D-printed ECM scaffolds 100. Further, FIG. 1A, FIG. 1B, FIG. 1C, and FIG. 1D show a panel 110 that is a magnified view of the respective 3D-printed ECM scaffolds 100 showing the surface texture.

The polymer material in the presently disclosed ECM mixture can be any biocompatible polymer, such as, but are not limited to, polyvinyl alcohol (PVA), polylactic acid (PLA), ethylene vinyl alcohol (EVOH), poly(lactide-co-glycolide) (PLGA), polyglycolide (PGA), nylon, polyketone, polyether ether ketone (PEEK), polyethylene terephthalate (PET), polyvinylidine chloride (PVDC), polyacrylonitrile (PAN), polyamides (PAs), polyvinyl chloride (PVC), polyvinylidene fluoride (PVDF), polyethylenimine (PEI), polycarbonate (PC), ethylene chlorotrifluoroethylene (ECTFE), polyethylene naphthalene (PEN), polytrimethylene terephthalate (PTT), liquid crystal polymers (e.g., Kevlar), nanocellulose, poly(methylmethacrylate (PMMA), and polybutylene terephthalate (PBT); as well as any biodegradable polymer, such as, but are not limited to, poly-(acid anhydride) (PAA), poly(butylene succinate) (PBS), poly(α-cyanoacrylate) (PCA), poly(ε-caprolactone) (PCL), poly(DL-lactide) (PDLLA), poly(DL-lactic acid), poly(ester amide) (PEA), poly(ester carbonate) (PEC), poly(ethylene succinate) (PES), poly(glycolide) (PGA), poly(glycolic acid), poly(glycolideco-lactide) (PGALA), poly(glycolic acid-co-lactic acid), poly(hydroxyalkanoate) (PHA), poly(3-hydroxybutyrate) (PHB), poly(L-lactide) (PLLA), poly(L-lactic acid), and poly(orthoester) (POE).

In one example of the presently disclosed ECM mixture, decellularized bone or cartilage particulates are mixed with polycaprolactone (PCL) or another biocompatible polymer material. PCL is a biodegradable polyester with a low melting point of around 60° C. and a glass transition temperature of about −60° C. The material, when heated above 60° C., becomes a viscous liquid PCL suspension with bone particulates that can be extruded from an extrusion-based 3D printer. This characteristic allows for the construction of anatomically shaped, porous, and patient-matched scaffolds with innate bioactivity that can be used to regenerate bone. By combining native bone with a biocompatible polymer material, manufacturability and bioactivity can both be attained using a single approach.

Referring now to FIG. 2 is a plan view of an example of a standard 3D-printed scaffold 200 formed without bone ECM material. Namely, the standard 3D-printed scaffold 200 is formed of 100% polymer material. FIG. 2 also shows a panel 205 that is a magnified view of the struts of the standard 3D-printed scaffold 200 and a panel 210 that is a magnified view of the standard 3D-printed scaffold 200 showing the surface texture.

Referring now to FIG. 3 is a plot 300 of the print quality of the presently disclosed 3D-printed ECM scaffolds 100 shown in FIG. 1A, FIG. 1B, FIG. 1C, and FIG. 1D as compared with the standard 3D-printed scaffold 200 shown in FIG. 2. For example, plot 300 shows a point P1 of the print quality of the 5%-3D-printed ECM scaffold 100 of FIG. 1A, a point P2 of the print quality of the 30%-3D-printed ECM scaffold 100 of FIG. 1B, a point P3 of the print quality of the 70%-3D-printed ECM scaffold 100 of FIG. 1C, a point P4 of the print quality of the 85%-3D-printed ECM scaffold 100 of FIG. 1D, a point P5 of the print quality of the standard 3D-printed scaffold 200 shown in FIG. 2. It is desirable that a suitably high print quality be maintained (on the order of the standard 3D-printed scaffold 200) in the presence of a high percent of bone ECM material in the 3D-printed ECM scaffold 100, as a high concentration of bone ECM material best promotes bone regeneration. For example, plot 300 shows a suitably high print quality for the 5%-3D-printed ECM scaffold 100, the 30%-3D-printed ECM scaffold 100, and the 70%-3D-printed ECM scaffold 100. The print quality, however, drops off somewhat for the 85%-3D-printed ECM scaffold 100.

One of ordinary skill in the art would recognize that many types of 3D manufacturing processes can be used to prepare the presently disclosed 3D-printed ECM scaffolds. Such processes generally are referred to as "additive manufacturing" processes, which have been classified into seven different categories by the American Society for Testing and Materials (ASTM) group "ASTM F42-Additive Manufacturing", Standard Terminology for Additive Manufacturing Technologies, 2012. These categories include "vat photopolymerisation," which uses a vat of liquid photopolymer resin., out of which the model is constructed layer by layer; "material jetting," which creates objects in a similar method to a two dimensional ink jet printer in which material is jetted onto a. build platform using either a continuous or Drop on Demand (DOD) approach; "binder jetting," which uses two materials, a powder based material and a binder. In such processes, the binder is usually in liquid form and the build material in powder form. A print head moves horizontally along the x and y axes of the machine and deposits alternating layers of the build material and the binding material; "fused deposition modelling" (FDM), which is a common material extrusion process in which material is drawn through a nozzle where it is heated and is then deposited layer by layer. The nozzle can move horizontally and a platform moves up and down vertically after each new layer is deposited. The FDM process can use a reel of filament, which once deposited, will adhere to underlying layers and neighboring filaments; a "powder bed fusion" process, which includes the following commonly used printing techniques: direct metal laser sintering (DMLS), electron beam melting (EBM), selective heat sintering (SHS), selective laser melting (SLM), and selective laser sintering (SLS); "sheet lamination" processes, which include ultrasonic additive manufacturing (UAM) and laminated object manufacturing (LOM). The UAM process uses sheets or ribbons of metal, which are bound together using ultrasonic welding; and "directed energy deposition" (DED) which covers a range of terminology including laser engineered net shaping, directed light fabrication, direct metal deposition, and 3D laser cladding. DED is a more complex printing process commonly used to repair or add additional material to existing components.

In particular embodiments, the 3D printing process comprises a FDM process. In yet more particular embodiments, the process comprises mixing the ECM/polymer; creating a filament, e.g., a filament 2.85 mm or 1.75 mm in dimeter; and feeding the filament into a 3D printer. The mixture of ECM/polymer can be in any form including, but not limited to, a pellet, a powder, a solution, and a filament. In even more particular embodiments, pellets comprising between about 30% to about 80% ECM, including 30%, 35%, 40%, 45%, 50%, 55%, 60%, 65%, 70%, 75%. and 80%, can be prepared. In yet even more particular embodiments, filaments comprising between about 30% to about 40% ECM can be prepared. Referring now in FIG. 10 is a representative filament produced by a FDM process.

Referring now to FIG. 4A and FIG. 4B are bar graphs indicating the mechanical characteristics of the presently disclosed 3D-printed ECM scaffolds 100. For example, FIG. 4A is a bar graph 400 of isotropic bulk material with respect to the mechanical characteristics of the 3D-printed ECM scaffolds 100. The bar graph 400 shows the compressive strength and Poisson's ratio of the bulk material printed without any pores. FIG. 4B is a bar graph 405 of transversely isotropic bulk scaffolds with respect to the mechanical characteristics of the 3D-printed ECM scaffolds 100. The bar graph 405 shows the mechanical properties (compressive modulus in x and z directions) and torsional modulus of the porous scaffolds.

Referring now to FIG. 5A, FIG. 5B, and FIG. 5C is a plot and bar graphs indicating the cell adhesion characteristics of the presently disclosed 3D-printed ECM scaffolds 100. For example, FIG. 5A is a plot 500 indicating the functional groups present on the surface of the 3D-printed ECM scaffolds 100. The plot 500 shows characteristic phosphate groups and collagen bonds on the surface of the 3D-printed ECM scaffolds 100. FIG. 5B is a bar graph 505 indicating the surface topography characteristics of the 3D-printed ECM scaffolds 100 as determined by atomic force microscopy (AFM). The bar graph 505 shows root-mean-square roughness of the surfaces as measured by AFM. FIG. 5C is a bar graph 510 indicating the cell adhesion characteristics of the 3D-printed ECM scaffolds 100. The bar graph 510 shows the strength of adhesion of adipose-derived stem cells seeded on 3D printed surfaces.

Referring now to FIG. 6A, FIG. 6B, FIG. 6C, and FIG. 6D are bar graphs with respect to in vitro osteoinductivity of the presently disclosed 3D-printed ECM scaffolds 100. For example, a bar graph 600 of FIG. 6A shows the relative expression of the transcription factor, Runx2, expressed by adipose-derived stem cells seeded into porous 3D-printed ECM scaffolds 100. A bar graph 605 of FIG. 6B shows the relative expression of the endocrine factor, osteocalcin, expressed by adipose-derived stem cells seeded into porous 3D-printed ECM scaffolds 100. A bar graph 610 of FIG. 6C shows the relative expression of the bone specific factor, osteonectin, expressed by adipose-derived stem cells seeded into porous 3D-printed scaffolds 100. A bar graph 615 of FIG. 6D shows the relative expression of calcium deposition by adipose-derived stem cells seeded into porous 3D-printed scaffolds 100 when cultured in medium that did not contain soluble phosphate (no phosphate) or medium that did contain soluble phosphate (with phosphate).

Referring now to FIG. 7 are plan views of the 30%-3D-printed ECM scaffold 100 and the 70%-3D-printed ECM scaffold 100 as compared with the standard 3D-printed scaffold 200 after six weeks in vivo and after twelve weeks in vivo. Here is demonstrated a 4-mm diameter critical-sized bone defect created in the cranium of immunocompromised mice and filled with 3D-printed scaffolds seeded with human adipose-derived stem cells. Mineral deposition is observed to various extents in scaffolds with 0%, 30%, and 70% bone ECM.

Referring now to FIG. 8 is a bar graph 800 of the amount of mineral deposited in the critical sized bone defects in the mice with respect to the 30%-3D-printed ECM scaffold 100, the 70%-3D-printed ECM scaffold 100, and the standard 3D-printed scaffold 200 shown in FIG. 7, which are after six weeks in vivo and after twelve weeks in vivo. The bar graph 800 shows the amount of mineral deposited at 6 weeks in the pore spaces of the scaffolds implanted into the critical-sized bone defects.

Referring now to FIG. 9 is a flow diagram of an example of a method 900 of making the presently disclosed ECM scaffolds 100. The method 900 may include, but it not limited to, the following steps.

At a step 910, tomography images of the patient's bone or organ are captured. For example, the tomography images of the patient's bone are captured using a computerized tomography scanner.

At a step 915, a mixture of the ECM material and polymer material is provided according, for example, to Table 1. In one example, the ECM mixture can comprise from about 5% to about 85% by weight of the ECM material, including 5%, 10%, 15%, 20%, 25%, 30%, 35%, 40%, 45%, 50%, 55%, 60%, 65%, 70%, 75%, 80%, and 85%, and from about 15% to about 95%, including 15%, 20%, 25%, 30%, 35%, 40%, 45%, 50%, 55%, 60%, 65%, 70%, 75%, 80%, 85%, 90%, and 95%, by weight of a polymer material. In another example, the ECM mixture can comprise from about 30% to about 75% by weight of the ECM material and from about 25% to about 70% by weight of a polymer material. In yet another example, the bone ECM mixture can comprise about 70% by weight of the ECM material and about 30% by weight of a polymer material.

At a step 920, the computerized tomography images are used to inform a manufacturing process of the anatomically-shaped porous ECM scaffold. In one example, the computerized tomography images are used to inform a 3D printing process for forming the ECM scaffold 100. In another example, the computerized tomography images are used to make molds for forming the ECM scaffold 100 using an injection molding process.

At a step 925, the anatomically-shaped porous ECM scaffold 100 is formed using the ECM mixture. In one example, the anatomically-shaped porous ECM scaffold 100 is formed by a 3D printing process. In another example, the anatomically-shaped porous ECM scaffold 100 is formed by an injection molding process. In any case, the ECM mixture (of Table 1) is heated to the appropriate temperature for processing.

summary, using the ECM mixtures shown in Table 1 and the method 900, anatomically-shaped, porous scaffolds comprised primarily of extracellular matrix can be provided. The gross geometry can be extracted from computerized tomography images and made in the shape of the patient's bone or organ. The pore sizes and geometry can be controlled to optimize tissue ingrowth and bone or organ regeneration. Most importantly the presently disclosed hybrid ECM/polymer scaffolds combine the manufacturability of synthetic materials with the bioactivity of native materials.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLE 1

Extrusion-Based Three-Dimensional Printing of Porous Bone Extracellular Matrix Scaffolds Methods. Bovine trabecular bone from 0.5 to 4-month-old calves was harvested with a 4-mm diameter drill core and decellularized via established protocols using a high-velocity water jet to remove the marrow, followed by detergent and enzymatic washes to remove residual cellular and nucleic acid material. Decellularized bone cores were then pulverized in a SPEX SamplePrep cryo-mill for 10 minutes at 10 cycles per second. The resulting bone powder was filtered through a 40-μm mesh to remove larger particles; this step was done to minimize risk of printer nozzle blockage by large bone particles. PCL with molecular weight 43 kg/mol to 50 kg/mol also was cryo-milled, but no size-exclusion filter was performed as the PCL melts and there is no risk of nozzle blockage. Bone and PCL powder were mixed together at bone:PCL ratios of 0%, 5%, 30%, 73%, and 85% by mass and porous lattices were printed. To confirm presence of bone matrix within the printed lattices, Alizarin Red S staining was performed post-printing. To quantify 'printability' of the different mixtures, printed lattices were compared pixel-by-pixel to a computer-generated "perfect" lattice. The percentage of matching pixels was termed "correlation factor."

To determine the osteoinductivity of hybrid scaffolds, scaffolds containing bone were seeded with adipose-derived stem cells (ASCs) embedded in fibrin gels and cultured under osteogenic or control conditions for seven days. Control medium consisted of Dulbecco's Modified Eagle Medium (DMEM) with 1 g/L glucose supplemented with 6% v/v fetal bovine serum (FBS) and 100 U/mL penicillin/100 μg/mL streptomycin while osteogenic medium consisted of control medium with the addition of 10 mM β-glycerophosphate and 50 μM ascorbic acid. Control groups with pure PCL scaffolds were cultured under the same conditions. At the end of 1 week, real-time polymerase chain reaction (RT-PCR) was performed on the osteogenic genes Runx2, osteocalcin, and osteonectin using β-actin as housekeeping gene.

Results: Printed hybrid lattices routinely stained positively for Alizarin Red S, with visibly more positive staining correlating with higher ratios of bone to PCL (see FIG. 11). In contrast, pure PCL scaffolds did not stain under Alizarin Red S (FIG. 11A). By gross observation, the printed struts from 0% to 30% bone were crisp and cylindrical, whereas strut geometry was irregular at 73% and 85% bone. Strut geometry was sufficiently irregular at 85% as to prohibit stacking of layers above layer 2 of printing. Quantification of pixel-by-pixel correlation (FIG. 12) confirmed these observations, with the correlation factor only slightly dropping up to the 73%-bone group, but markedly falling at 85%-bone ECM. With these observations, all subsequent studies were done using 73% bone:PCL by mass. RT-PCR showed a significant increase in the expression of osteogenic genes Runx2, osteocalcin, and osteonectin in cells cultured in 73% bone scaffolds as compared to cells cultured in pure PCL scaffolds, indicating the incorporated mineral has an osteoinductive effect on resident cells.

Discussion. While the gold standard for bone engineering scaffolds remains the decellularized trabecular bone matrix due to the innately osteoinductive property of native bone, the use of decellularized tissue for scaffolds suffers from several major drawbacks. Clinically relevant volumes of decellularized bone are difficult to obtain, especially for critically sized bone defects that require bone engineering. Decellularization of large volumes of bone also is difficult and may require specialized perfusion apparatus for chemical and mechanical decellularization agents to reach the inner regions of the tissue. Finally, the shaping of native bone to appropriate anatomical shapes, a critical consideration for craniofacial bone reconstruction, is challenging. By cryo-milling bone into smaller particles and mixing the resulting bone powder into a greater PCL phase, many of these drawbacks are overcome. It is no longer necessary to obtain large, continuous volumes of bone, as the bone will be ground into particles. As a result, smaller pieces of bone can be obtained and much more easily decellularized prior to milling. After the mixture of bone and PCL is obtained at the desired concentration, the approach described herein uses highly versatile 3D printing processes to produce anatomical shapes with high fidelity, a procedure that is impossible to apply to native bone alone.

Summary. The combination of 3D printing technologies with the use of decellularized bone matrix synergizes the ability to produce complex anatomical shapes having the bioactivity of native tissue. In particular, the use of native bone matrix captures both mineral and organic components of native bone, potentially resulting in a scaffold that is more osteoinductive and osteoconductive than current bioinert synthetic scaffolds or scaffolds incorporating only mineral components, such as hydroxyapatite.

EXAMPLE 2

Three-Dimensional Printing of Bone Extracellular Matrix for Craniofacial Regeneration Overview. Tissue-engineered approaches to regenerate bone in the craniomaxillofacial region utilize biomaterial scaffolds to provide structural and biological cues to stem cells to stimulate osteogenic differentiation. Bioactive scaffolds are typically comprised of natural components, but often lack the manufacturability of synthetic materials. To circumvent this trade-off, the presently disclosed subject matter provides 3D printed materials comprised of decellularized bone (DCB) matrix particles combined with polycaprolactone (PCL) to create hybrid DCB:PCL scaffolds for bone regeneration. Hybrid scaffolds were readily printable at compositions of up to 70% bone by mass and displayed robust mechanical properties. Assessments of surface features revealed both collagenous and mineral components of bone were present. Qualitative and quantitative assessments showed increased surface roughness relative to that of pure PCL scaffolds. These findings correlated with enhanced cell adhesion on hybrid surfaces relative to that on pure surfaces. Human adipose-derived stem cells (hASCs) cultured in DCB:PCL scaffolds without soluble osteogenic cues exhibited significant upregulation of osteogenic genes in hybrid scaffolds relative to pure PCL scaffolds. In the presence of soluble phosphate, hybrid scaffolds resulted in increased calcification. The hASC-seeded scaffolds were implanted into critical-sized murine calvarial defects and yielded greater bone regeneration in DCB:PCL scaffolds compared to that in PCL-only at 1 and 3 months post-transplantation. Taken together, the presently disclosed results demonstrate that 3D printed DCB:PCL scaffolds might be effective for stimulating bone regeneration.

Background Craniomaxillofacial (CMF) injuries, resulting from congenital defects, (Parker, et al., 2010) trauma, (Breeze, et al., 2011) and surgical resection, (Wei, et al., 1994) are a significant clinical challenge. CMF injuries negatively impact patient speaking ability, eating behaviors, and psychosocial well-being. Approximately 200,000 CMF injuries occur annually, incurring a significant economic burden. (Desai, 2007)

The current gold standard for CMF repair is the autologous vascularized free fibular flap; (Brydone, et al., 2011; Broyles, et al., 2014) however, this technique relies on a limited source of donor tissue and incurs donor-site morbidity. In addition, the complex geometries of bone within the CMF region cannot be easily recapitulated using fibular segments. Although prosthetic implants have been investigated, no single method presents an ideal solution. (Reddy, et al., 2014) The widely used poly[methyl methacrylate] implant has disadvantages in its highly exothermic synthesis, which can lead to tissue necrosis in the CMF region, as well as its brittle mechanical properties. (Benzel, et al., 1990).

Another widely used material, titanium, has superior mechanical properties, but has high costs and low hard-tissue integration with native bone; (Park, et al., 2001) furthermore, it carries risks of soft tissue dehiscence and inflammation. Finally, the use of prosthetic implants in younger patients, whose tissue continues to grow, remains a challenge as multiple revision surgeries are needed to accommodate the growing tissue. Tissue engineering of bone presents a possible solution to these drawbacks. Traditionally, bone progenitor cells are combined with a biomaterial scaffold and signaled with appropriate bioactive factors to create a construct that will regenerate lost tissue. (Langer, et al., 1993)

The ideal tissue engineering approach to repairing CMF defects would result in a completely biological tissue that is capable of adapting to physiological cues, overcoming the limitation of prosthetics. Although bone engineering approaches have enjoyed several advancements, the choice of the scaffold is still associated with several challenges. For CMF bone, this biomaterial scaffold is critical, as it determines mechanical properties and tissue geometry. Current materials used to engineer scaffolds fall into two general categories: naturally derived and synthetic. Although several naturally derived materials have been used in bone engineering, such as collagen sponges (Iejima, et al., 2003) and chitosan, (Ucar, et al., 2013) the gold standard for bone scaffolds within tissue engineering is allogenic decellularized trabecular bone (DCB), notable for its intrinsic osteoinductivity, osteoconductivity, and appropriate mechanical properties. (Urist, et al., 1965; Urist, et al., 1979; Sampath, et al., 1984; Harakas, 1984) As a result, DCB scaffolds have been widely used in bone engineering investigations. (Mauney, et al., 2004; Mauney, et al., 2005; Marcos-Campos, et al., 2012; Gerhardt, et al., 2013; Hung, et al., 2013)

To this end, DCB scaffolds in the shape of the temporomandibular joint condyle have been previously produced, demonstrating the potential for these scaffolds in recapitulating complex CMF geometries. (Grayson, et al., 2010). Despite recapitulating the appropriate anatomic geometry, obtaining clinically relevant and continuous volumes of trabecular bone for scaffold production is challenging. To overcome these limitations, synthetic scaffolds have been produced using various biomaterials, such as poly[lactic acid] and poly[glycolic acid]. (Saito, et al., 2013)

Notably, synthetic scaffolds can harness the capabilities of fabrication via three-dimensional printing, (Eshraghi, et al., 2010; Park, et al., 2012) a particular advantage for bone engineering in the CMF region due to the complex geometries in this region. Polycaprolactone (PCL) scaffolds fabricated in the shape of the mandible and maxilla via 3D-printing have been reported, demonstrating the potential of this technology for producing CMF geometries of a size scale above that possible using DCB scaffolds. (Temple, et al., 2014). In particular, the relatively low melting point of PCL, 60° C., makes it well-suited to extrusion-based 3D printing.

Although this approach is promising, synthetic scaffolds lack the osteoinductivity and osteoconductivity of naturally derived scaffolds. Functionalizing synthetic scaffolds to impart bioactivity, such as by incorporating appropriate osteoinductive growth factors (Yilgor, et al., 2010) or incorporation of mineral phases, (Oliveira, et al., 2009; Azami, et al., 2010; Umeda, et al., 2007; Nienhuijs, et al., 2010) has had some success in overcoming this challenge; however, these approaches do not recapitulate the full bioactivity of DCB scaffolds. Namely, they do not include the collagenous phase of bone, which has been shown to enhance osteogenesis in dogs when combined with tricalcium phosphate implants compared to that with tricalcium phosphate alone. (Baas, et al., 2008). Previous studies using collagen in conjunction with bone scaffolds resulted in increased cell migration throughout the scaffold. (Hung, et al., 2013). Without wishing to be bound to any one particular theory, it was thought that by incorporating DCB particles into PCL, a hybrid DCB:PCL material could be created that incorporates both mineral and collagenous bioactive phases of bone, maintains the osteoinductive and osteoconductive properties of DCB, and is readily manufactured by 3D printing.

Accordingly, the presently disclosed subject matter (1) evaluates the print quality of 3D-printed hybrid scaffolds at different DCB:PCL ratios, (2) determines the mechanical properties of hybrid scaffolds, (3) characterizes the ability of human adipose-derived stem cells (hASCs, a cell type used successfully in bone engineering applications) to adhere to the DCB:PCL hybrid material, (4) assesses the ability of DCB:PCL scaffolds to differentiate resident hASCs to bone, and (5) assesses the ability of the DCB:PCL material to regenerate bone in an orthotopic cranial defect.

Experimental

Creation of Hybrid Material. Trabecular bone was obtained from the subchondral region of 0.5-4 month old calves. Decellularization proceeded as previously described. (Hung, et al., 2013; Correia, et al., 2011). Bone was first subjected to a high-pressure water jet to wash out the marrow. Then, bones were washed with phosphate-buffered saline (PBS; Cellgro, Manassas, Va) containing 0.1% w/v ethylenediaminetetraacetic acid (EDTA; Sigma-Aldrich, St. Louis, Mo) for 1 h at room temperature and then overnight with PBS containing 0.1% w/v EDTA and 10 mM Tris (Sigma-Aldrich) at 4° C. Bones were then washed for another hour in PBS before being subjected to a wash consisting of PBS with 10 mM Tris and 0.5% sodium dodecyl sulfate (SDS; Sigma-Aldrich) for 1 day at room temperature. The SDS was removed with extensive PBS washes and then the bones were washed with PBS containing 10 mM Tris, 50 U/mL DNase (Roche Applied Science, Indianapolis, Ind.), and 1 U/mL RNase (Roche Applied Science) for 5 h at room temperature. Enzymes were removed with extensive PBS and water washes before storage via lyophilization. Decellularized trabecular bone was pulverized using a SPEX SamplePrep 6770 cryo-mill (SPEX SamplePrep, Metuchen, NJ) at a frequency of 10 Hz for 15 min to obtain bone particles. The particles were then run through a 40-µm cell strainer to confine maximum particle size to 40 µm, a step performed to minimize risk of particle aggregation and clogging of the printer nozzle. This size of particles was confirmed via scanning electron microscopy (SEM; FIG. 23). The resulting bone particles were mixed with PCL powder with molar mass of 43000-50000 g/mol (Polysciences Incorporated, Warrington, PA) for printing.

Scaffold Fabrication and Evaluation of Print Quality. Hybrid mixtures consisting of 0%, 5%, 30%, 70%, and 85% bone by mass were created and printed at 80° C. into 0.644 mm height (2 layer), 4-mm diameter scaffolds of 60% porosity using our custom 3D printer. (Temple, et al., 2014). These parameters resulted in strut diameters of 460 µm and pore sizes were approximately 800 µm. This geometry was chosen to be consistent with the geometry required for the in vivo studies outlined herein below. Scaffold pore size was selected due to optimizations performed in a previous study in which 60% porosity was shown to yield the most uniform cell distribution during seeding. (Temple, et al., 2014). Scaffolds were stained with Alizarin Red S (Sigma-Aldrich) to confirm the presence of mineralized particles and imaged under brightfield and scanning electron microscopy. Low-magnification brightfield images of scaffolds were compared pixel-by-pixel to a computer-generated ideal lattice. The percentage of pixels that matched between the two images was normalized to 50% to account for random matching, and this numerical score, ranging from 0 to 100, was taken as a measure of print quality.

Raman Spectroscopy. For determining the molecular constituents of the hybrid material and confirming the presence of both the mineral and collagen phases of the DCB particles, Raman spectroscopy was utilized as previously described. (Sathyavathi, et al., 2015). Briefly, an 830-nm laser (Process Instruments, Salt Lake City, UT) was used to deliver light to a sheet consisting of 30% bone by mass. Background subtraction and normalization was performed using a barium sulfate spectrum, and wavenumber assignment was performed using a Tylenol spectrum. As controls, the spectra of pure PCL and a block of decellularized trabecular bone also were obtained.

Atomic Force Microscopy. To determine the surface roughness of the hybrid material, atomic force microscopy (AFM) was performed on printed sheets of 0%, 30%, and 70% bone by mass using a Dimension 3100 AFM (Bruker Nano, Santa Barbara, CA) in tapping mode with Bruker Nano probe model RTESPW. The root-mean-square roughness of nine 2 µm×2 µm square regions on each sample surface was measured at 15 Hz and averaged to determine the roughness of that sample. A total of three sample surfaces were tested for each DCB concentration.

Mechanical Testing. Solid cubes of 0%, 30%, and 70% bone by mass, 1.25 cm on all sides, were printed and subjected to unconfined compression using an EnduraTEC ELF 3200 system (Bose Corporation, Framingham, Mass.). As the specimens were solid, mechanical properties were assumed to be isotropic, and compression of up to 5% static strain was applied along the print axis, termed the z-axis, to determine the compressive modulus of the bulk material. Resulting expansion along the perpendicular x-axis also was measured to determine the Poisson's ratio. Three blocks for each DCB concentration were tested. For measuring scaffold properties, porous cubes of 60% porosity and 1.25 cm on all sides were also printed. Because of the print layers, the properties along the z-axis differ from those of the other two axes; thus, the mechanical properties were assumed to be transversely isotropic. As such, compressive moduli were measured in both the z- and x-directions. Shear moduli also were measured with respect to the x-face along the z-direction. Three porous cubes for each DCB concentration were tested.

Measurement of Cell Adhesion Strength. As a measure of cell interaction with the hybrid material, the strength of cell adhesion to the hybrid material was quantified by a modification of a centrifugation assay described previously. (Hung, et al., J. Biomed. Mater. Res., Part A, 2013; Reyes, et al., 2003). Briefly, fluorescently labeled cells were allowed to adhere to printed sheets of 0%, 30%, and 70% bone by mass for 24 h. Sheets were affixed onto a glass microscope slide using cyanoacrylate glue with the cells facing away from the slide. Slides were then immersed in PBS and subjected to centrifugation at different speeds. The position of the sheet on the slide relative to the centrifuge rotor, as well as the centrifugation speed determined the shear stress applied to the cells (Hung, et al., J. Biomed. Mater. Res., Part A, 2013):

$$\sigma = \|\vec{\omega}\|^2 \, y r_r \, (\Delta \rho) \tag{1}$$

where $\sigma$ is the shear stress, $\vec{\omega}$ is angular velocity of the centrifuge where double bars denote vector magnitude, y is the average height of adhered cells as determined by microscopy, $r_r$ is the distance from the rotor of the centrifuge, and $\Delta \rho$ is the difference in density between a cell and the surrounding PBS. The fraction of remaining cells after each spin was plotted against the shear stress applied during that spin, and these data were fit to a variable-slope concentration response model (VSCR; eq 235, (Sauermann, et al., 1998; Feuerstein, et al., 1999)) to obtain a value for $\sigma 50$, the shear required for 50% of the cells on the sheet to detach:

$$f = \frac{\sigma^a}{\sigma^a + \sigma_{50}^a} \tag{2}$$

where f is the fraction of cells adhered and $\alpha$ is a cooperativity coefficient of detachment. Four sheets composed of each DCB concentration were tested and the four values of $\sigma_{50}$ were averaged for each material composition.

Measurement of Osteoinductivity. For measuring the ability of hybrid scaffolds to induce resident cells to undergo osteogenesis, hASCs of passage 2 were seeded into fibrin gels at 20 million cells per milliliter, and 5µL gels were implanted into scaffolds of 0, 30, and 70% DCB by mass. Seeding proceeded as previously described (Hung, et al., 2015) with a fibrinogen concentration of 10 mg/mL, thrombin concentration of 10 U/mL, and volume ratio of 4:1 fibrinogen/thrombin for a final fibrinogen concentration of 8 mg/mL and a final thrombin concentration of 2 U/mL. Scaffolds were 0.644 mm in height, 4 mm in diameter, and had 60% porosity. Scaffolds were sterilized by ethanol wash for 1 h at room temperature. hASCs were obtained as described previously. (Hung, et al., 2015; Estes, et al., 2010; Hutton, et al., 2014). All lipoaspirates obtained to isolate hASCs were obtained under Institutional Review Board approved protocols with patient consent. Briefly, lipoaspirate was digested with 1 mg/mL of collagenase I (Worthington Biochemical Corporation, Lakewood, NJ) for 1 h at 37° C. The released cells were centrifuged to obtain the stromal vascular fraction pellet and plated. Adherent cells were termed hASCs and expanded for the current study. Expansion conditions consisted of Dulbecco's modified Eagle medium (DMEM; Life Technologies, Frederick, Md.) with 4.5 g/L of glucose, 10% v/v fetal bovine serum (FBS; Atlanta Biologicals, Flowery Branch, Ga.), 100 U/mL of penicillin, 100 µg/mL of streptomycin (Cellgro), and 1 ng/mL of basic fibroblast growth factor (PeproTech, Rocky Hill, NJ). The hASCs from a single donor were used for all experiments.

After seeding into scaffolds of 0, 30, and 70% DCB by mass, constructs were cultured for 1 and 3 weeks under control conditions: DMEM with 1 g/L of glucose, 100 U/mL of penicillin, 100 µg/mL of streptomycin, and 6% v/v FBS. The absence of osteoinductive factors ensured that only the scaffold could induce osteogenesis within resident cells. The sample size was n=3 for each DCB concentration at each time point. After the culture periods, cells were digested with TRIzol (Life Technologies), and isolated mRNA was used to produce cDNA. cDNA was subject to real-time polymerase chain reaction (RTPCR) for the osteogenic genes Runx2, osteocalcin (OCN), and osteonectin (ON) as previously described. (Hung, et al., 2015) For analysis, the delta-delta Ct method was used in which β-actin served as the housekeeping gene and gene expression under pure PCL scaffolds served as the control group. As an additional measure of osteoinductivity, constructs also were cultured for 3 weeks under osteogenic conditions, which consisted of control conditions supplemented with 10 mM β-glycerophosphate (Sigma-Aldrich) and 50 µM ascorbic acid (Sigma-Aldrich). These constructs were subject to the Quant-It PicoGreen dsDNA assay (Invitrogen, Carlsbad, CA) and the Stanbio LiquiColor calcium assay (Stanbio, Boerne, TX) to determine calcium content normalized to cell number as previously described. (Hung, et al., 2015)

In Vivo Assessment of Bone Regeneration. For determining the effect of the hybrid scaffolds in vivo, the critically sized murine calvarial defect model was used as previously described. (Hung, et al., 2015; Cowan, et al., 2004; Gupta, et al., 2008). All procedures were reviewed and approved by the Johns Hopkins Animal Care and Use Committee. Briefly, a 4-mm circular knife (Medicon, Tuttiligen, Germany) was used to excise a 4-mm disk of calvaria between the coronal and lambdoid sutures 1 mm lateral to the sagittal suture with care taken to preserve the underlying dura mater. This size has been shown previously to be nonhealing. (Hung, et al., 2015; Cowan, et al., 2004; Gupta, et al., 2008). Constructs consisting of hASCs seeded in fibrin inside scaffolds of 0%, 30%, and 70% bone by mass created as in the previous section were immediately implanted into the resulting defect.

A total of 12 mice were operated on with n=4 for each concentration of bone. The contralateral side served as unoperated controls. Mice were imaged under computed tomography (CT) using a Gamma Medica X-SPECT small animal system (Gamma Medica, Salem, N.H.) at 6 and 12 weeks postimplantation. Imaging was performed at 80 kV peak voltage and 600 µA current. Reconstruction was done with a voxel size of 100 µm. At 12 weeks postimplantation, scaffolds were excised and fixed under 3.7% formalin overnight for histological analysis as previously described. (Hung, et al., 2015). Histological analysis consisted of a hematoxylin and eosin (H&E) stain for cellularity (Sigma-Aldrich) and a von Kossa and van Gieson stain for bone formation (Sigma-Aldrich).

Results

Print Quality. DCB:PCL scaffolds of 0%, 5%, 30%, 70%, and 85% bone by mass were printed and stained with Alizarin Red S. Staining in all scaffolds was observed except in the 0% scaffold, where no mineral was present, confirming the presence of bone particles within the hybrid scaffolds. The intensity of the red stain increased with increasing DCB concentration (FIG. 17). When compared to a computer-generated ideal lattice, the print quality decreased as the concentration of bone increased from a score of roughly 89 for 0% and 5% DCB scaffolds to 77.6 for 70% DCB scaffolds; however, a dramatic drop in score (50) was observed at 85% DCB (Table 2). As such, for all subsequent studies, 70% bone by mass was chosen as the maximum concentration of bone; 0% bone by mass was chosen as a pure PCL control, and 30% bone by mass was chosen as an intermediate uroub.

TABLE 2

Measurement of Print Quality

| concentration of bone (% mass) | print quality (—) |
| --- | --- |
| 0 | 88.2 |
| 5 | 89.6 |
| 30 | 85.8 |
| 70 | 77.6 |
| 85 | 50.0 |

Raman Spectroscopy. To confirm whether mineral and collagen were present on the surfaces of 3D-printed DCB:PCL, Raman spectroscopy was employed (FIG. 18A, FIG. 18B, and FIG. 18C). Raman spectroscopy of a printed sheet of 30% bone by mass showed a peak at 960 $cm^{-1}$ corresponding to the phosphate component of bone and a peak at 1650 $cm^{-1}$ corresponding to the amide I signal from collagen. (Mandair, et al., 2015). These peaks appear in the Raman spectrum of trabecular bone but not in the spectrum for pure PCL (FIG. 18A), matching observations reported previously. (Taddei, et al., 2005).

The contributions from the PCL phase include the triple peak centered around 1450 $cm^{-1}$ for $\delta CH_2$ (fourth carbon from the carbonyl), the double peak at 1300 $cm^{-1}$ for $\omega CH_2$ (furthest carbon from the carbonyl), and the skeletal stretching peak at 1110 $cm^{-1}$, (Taddei, et al., 2005; Kister, et al., 2000) which are signals appearing in the spectra for both pure PCL (FIG. 18A) and the 30% bone by mass sample (FIG. 18C).

Atomic Force Microscopy. SEM revealed that the surfaces of the 30% and 70% scaffolds displayed more features than those of the 0% scaffolds, whose surfaces were mostly smooth (FIG. 17). For quantifying the surface roughness of scaffolds, which is known to affect cell-biomaterial interactions, (Dalby, et al., 2007; McNamara, et al., 2010; Hung, et al., Stem Cell Res. Ther., 2013) AFM was performed, and the root-mean-square roughness of 0%, 30%, and 70% scaffolds were computed. At the length scale of AFM, no significant differences were observed between 30 and 70% scaffolds: both had roughness values around 50 nm. Both 30% and 70% scaffolds were significantly rougher than were 0% scaffolds, which showed a surface roughness of 4.83 nm (FIG. 19A), confirming observations under scanning electron microscopy.

Mechanical Properties. To determine how the bone particles affected the mechanical properties of the bulk material, the compressive properties of the bulk material were tested. The 0% and 30% blocks had similar compressive moduli of around 30 MPa, whereas the 70% blocks showed a significant drop in modulus to around 10 MPa. The Poisson's ratio of approximately 0.3 did not differ significantly between the three groups (FIG. 4A). The same trend held for the compressive and shear moduli of 60% porous scaffolds. The compressive modulus in the x-direction was similar for both the 0% and 30% scaffolds at around 15 MPa, whereas the modulus for 70% scaffolds was around 7 MPa. In the z-direction, 0% and 30% scaffolds had moduli approaching 10 MPa, whereas the 70% scaffolds had moduli approaching 5 MPa (FIG. 4B).

Cell-Biomaterial Adhesion. Cell adhesion to the hybrid material as an indicator of cell-material interactions also was investigated. The centrifuge-applied shear successfully detached cells in a force-dependent manner, and the VSCR model (Hung, et al., J. Biomed. Mater. Res., Part A, 2013; Sauermann, et al., 1998; Feuerstein, et al., 1999) fit the data well (FIG. 20A). The shear for half-detachment, $\sigma_{50}$, was significantly different between all three groups (FIG. 20B), increasing in a concentration-dependent manner from 0.0872 Pa for pure PCL adhesion to 28.2 Pa for adhesion to 70% bone by mass. This observation is well-supported by the surface biomolecular data (FIG. 18A, FIG. 18B, and FIG. 18C) and the surface roughness data (FIG. 17, FIG. 19A, and FIG. 19B).

As an in vivo correlation that the observed concentration dependent trend occurs with cell invasion, acellular scaffolds were implanted in the murine calvarial defect and excised for H&E after 1 week. Although little cell invasion was observed in 0% scaffolds, a concentration-dependent increase in cell invasion occurred with increasing concentration of bone in hybrid scaffolds (FIG. 24). Taken together, these data confirm that hybrid scaffolds are more amenable to cell adhesion and migration when compared to those of pure PCL scaffolds.

In Vitro Osteoinductivity. The ability of hybrid scaffolds to induce resident cells to form bone also was examined. By 3 weeks of culture, Runx2 expression increased by more than 3 orders of magnitude whereas OCN and ON expression increased by approximately 5 orders of magnitude compared to PCL alone despite the absence of soluble osteoinductive factors in the culture medium (FIG. 6A, FIG. 6B, FIG. 6C, and FIG. 6D). Because no phosphate source was present, this increase in gene expression did not yield calcium production; however, when a phosphate source was added with ascorbic acid and constructs cultured for 3 weeks, the hybrid scaffolds displayed higher calcium production per cell relative to pure PCL controls with 70% scaffolds yielding 88.0 ng/cell and 30% scaffolds yielding 48.1 ng/cell compared to 35.3 ng/cell from pure PCL scaffolds (FIG. 6A, FIG. 6B, FIG. 6C, and FIG. 6D). Because little to no calcium was detected in samples with no phosphate, it can be surmised that the calcium content innately present in the hybrid scaffold was not being detected by the assay.

In Vivo Osteoinductivity. As a final assessment of the osteoinductive properties of hybrid scaffolds relative to those of pure PCL scaffolds, scaffolds of 0%, 30%, and 70% bone by mass were fabricated and seeded with hASCs as was done in the in vitro experiment. The resulting constructs were implanted in 4-mm murine calvarial defects. CT scans at both 6 and 12 weeks post implantation revealed that hybrid scaffolds invoked nearly twice the volume of regenerated bone compared to that from pure PCL scaffolds (FIG. 7 and FIG. 8) with hybrid scaffolds approaching 4 mm$^3$ of regenerated bone compared to 2.07 mm$^3$ regenerated bone with pure PCL scaffolds. The pattern of signal detected by CT within the defect suggested that the system was not picking up the mineral innately present within the hybrid scaffolds, as the detected bone was punctate and isolated rather than ubiquitously present within the scaffold struts (which were not visible under CT). CT scans also revealed that regenerated bone appeared in both the scaffold centers as well as from the edges, suggesting that implanted cells within the scaffold and invading cells from the host were both contributing to repair. Histological analysis (FIG. 21) revealed the presence of both nonmineralized osteoid and mineralized tissue, as visualized by the van Gieson and von Kossa stains, respectively, indicating that bone regeneration was actively occurring within the defect.

3D Printing of Anatomical Geometry. For demonstrating the ability of the approach described here to create anatomical shapes, the geometry of the human temporomandibular joint condyle was extracted and printed using pure PCL as well as 30% bone by mass. The scaffolds printed successfully and were subject to Alizarin Red S staining to confirm the presence of bone mineral (FIG. 22). Although the pure PCL condyle did not stain, as expected, robust staining was observed in the 30% bone by mass condyle, demonstrating that 3D printing of hybrid material can be used to fabricate complex craniofacial geometries.

Discussion

Hybrid scaffolds consisting of bone particles embedded in a greater polycaprolactone phase were printed using a custom 3D printer. This is the first time a bone engineering hybrid scaffold has been fabricated by 3D printing of naturally derived ECM. In addition to being readily printable, hybrid scaffolds are more amenable to cell adhesion compared to pure PCL scaffolds and are osteoinductive both in vitro and in vivo. As such, the hybrid material disclosed herein mitigates the lack of osteoinductivity and osteoconductivity in pure PCL while simultaneously overcoming the manufacturing challenges associated with producing a pure decellularized trabecular bone scaffold. Mechanics were considered as a potential limiting factor in the use of this hybrid material, as mechanical properties for bone engineering scaffolds are crucial due to the role of bone as a load-bearing tissue. The choice of PCL as a biomaterial partly arises from this consideration, as its mechanical properties (stiffness on the order of 107 Pa) fall within the range reported for trabecular bone of 0.5-14.6 MPa. (Ang, et al., 2007; Goldstein, 1987). Even with the drop in properties at 70% DCB by mass, the stiffness values reported for DCB:PCL scaffolds still approach the values of trabecular bone and are within the range reported in the literature for pure PCL 3D-printed scaffolds. (Zein, et al., 2002; Zhou, et al., 2007). Composite collagen/calcium phosphate-printed scaffolds were reported to have a modulus of approximately 15 MPa, comparable to the values in the present study; (Inzana, et al., 2014) however, it should be noted that the porosity in the presently disclosed scaffolds—an important property for highly osteoconductive scaffolds—is much greater in comparison while still retaining appropriate moduli. Taken together, these data suggest that mechanics is not a limiting factor in the use of these hybrid scaffolds in bone engineering.

Next, the interactions between human stem cells and the hybrid material were examined. Two important aspects of cell-biomaterial interactions were investigated: cell adhesion to biomaterials has been studied extensively and affects many aspects of cell behavior, whereas cell migration through a biomaterial scaffold is crucial for a uniformly seeded graft as well as for recruitment of host cells to the implant. The SEM and AFM data on surface roughness indicated that this was a feature of the printed hybrid material that could enhance cell adhesion at different length scales—the micrometer scale as shown under SEM and the nanometer scale as shown under AFM. Meanwhile, the presence of collagen as confirmed by Raman spectroscopy suggested that an increased number of binding sites could be a second mode by which the hybrid material could enhance cell adhesion. The data demonstrate increasing cell adhesion strength with higher concentrations of bone in the scaffolds. In comparison, the shear forces required for half-detachment of ASCs seeded on scaffolds containing 70% bone by mass (approximately 30 Pa) agrees well with previous studies on cell adhesion to hydroxyapatite. (Deligianni, et al., 2001). Although it should be noted that the values disclosed herein for initial cell numbers reflect a combination of initial adhesion and proliferation after 1 day, the trend that higher concentration of DCB leads to increased σ50, an effect of surface roughness, the presence of collagen, or both, remains true. The RT-PCR data are derived from ASCs grown in scaffolds in vitro and provide evidence that the hybrid scaffolds are innately osteoinductive. The RQ values reported are normalized to expression in pure PCL scaffolds, where no osteoinductive cues were present and little expression of osteogenic genes is expected. Interestingly, the osteogenic gene expression in hybrid DCB:PCL scaffolds increased compared to that in pure PCL scaffolds despite the absence of soluble osteoinductive factors in the culture medium. The observation that calcium per cell in pure PCL scaffolds matches closely with previously reported values (30-40 ng/cell (Hung, et al., 2015)) and increases in hybrid scaffolds demonstrates both the osteogenic capability of the cells, as well as the ability of the hybrid scaffold to enhance this capability. The changes in bone volume following transplantation of ASC-seeded scaffolds into orthotopic defects also supported the hypothesis that hybrid scaffolds are osteoinductive compared to pure PCL scaffolds. Note that in that particular experiment, the cells were not provided any soluble osteoinductive cues prior to implantation. Consequently, differentiation cues were provided solely by the DCB:PCL hybrid scaffolds. The percent of bone regenerated in the current study also is comparable to previous studies where PCL:tricalcium phosphate:collagen scaffolds were implanted into rat calvariae. (Sawyer, et al., 2009)

In examining the spatial profile of the bone formed, bone is visible both in the scaffold pore spaces and in the scaffold edges. As such, without wishing to be bound to any one particular theory, two factors could be at play: bone being regenerated from the implanted human cells, which are distributed throughout the scaffold and therefore can regenerate bone from the scaffold interior, as well as bone regenerated from endogenous murine cells as they migrate in from the scaffold periphery. It is worth noting that the hybrid scaffold potentially enhances both of these avenues of regeneration due to both mineral and collagenous phases enhancing osteoinductivity and osteoconductivity.

Although a printable, bioactive scaffold is disclosed herein, future optimizations may be performed. First, the particle size of DCB was chosen at a maximum of 40 µm in the current study to reduce the chance of particle aggregation blocking flow from the print nozzle, which has a diameter an order of magnitude above this size. This particle size resulted in successful prints of bioactive scaffolds; however, it is possible that smaller particle sizes may further increase the amount of bone that can be printed as nozzle clogging becomes less of an issue. Another effect of particle size is the nanotopography of the scaffold, which as is shown here is affected at the nanoscale despite the microscale of the particles. Nanoscale changes in topography have been shown to affect the expression of osteocalcin in MSCs (Dalby, et al., 2007), whereas the use of nanotopography to control cell shape was shown to modulate BMP-dependent osteogenesis (Wang, et al., 2012).

Another effect of particle-mediated nanotopography is the potential for the particles to serve as nucleation sites for the deposition of mineral, leading to enhanced bone formation. (Bhumiratana, et al., 2011). Taken together, this observation suggests that the DCB particle size alone also might play a role in enhancing the osteogenesis of seeded stem cells. Second, the method of printing chosen here, an extrusion based system, was selected due to its ease of use. Effectively, PCL was used as a "binder" to hold the DCB together. Other methods that have fabricated composite scaffolds, such as with synthetic ceramics, have used acidic binders that unfortunately result in decreased cell viability as well as smaller pore size due to the increased flow of acidic binders away from the target print location. (Inzana, et al., 2014). It has been shown that smaller pore size inhibits the migration and proliferation of seeded and infiltrating cells. (Stoppato, et al., 2013). As such, another advantage of the method used here is that PCL as the "binder" is readily printable, with minimal flow away from the target print location due to high viscosity, and is not cytotoxic. One potential shortcoming of this approach is the DCB is subject to 80° C. printing temperatures that destroy osteoinductive growth factors, such as BMP, that are known to reside in bone matrix; (Urist, et al., 1965; Urist, et al., 1979; Sampath, et al., 1981) however, many other methods of printing feature temperatures above this value, such as 1300° C. for sintering techniques. (Suwanprateeb, et al., 2009). Despite the elevated temperatures used in this study, the hybrid scaffolds produced by the presently disclosed methods were still shown to be osteoinductive, likely due to the presence of the mineral phase; furthermore, the collagenous phase of bone was retained as shown by Raman spectroscopy. As such, the hybrid scaffold still represents an increase in bioactivity from pure PCL scaffolds while retaining printability. For the first time, bone matrix can be 3D-printed into any of the complex shapes in the human skeleton, representing a potentially storable, patient-specific component to tissue engineered bone grafts.

Summary

A hybrid material consisting of bone extracellular matrix embedded in a greater polycaprolactone phase was developed. This material is 3D printable while displaying osteoinductive properties in vitro and in vivo as evidenced by gene expression, calcium per cell, and in vivo bone regeneration of seeded human adipose-derived stem cells.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein Ang, K. C.; Leong, K. F.; Chua, C. K.; Chandrasekaran, M. Compressive properties and degradability of poly(epsilon-caprolactone)/hydroxyapatite composites under accelerated hydrolytic degradation. J. Biomed. Mater. Res., Part A 2007, 80 (3), 655-60.

Azami, M.; Samadikuchaksaraei, A.; Poursamar, S. A. Synthesis and characterization of a laminated hydroxyapatite/gelatin nanocomposite scaffold with controlled pore structure for bone tissue engineering. Int. J. Artif. Organs 2010, 33 (2), 86-95.

Baas, J.; Elmengaard, B.; Bechtold, J.; Chen, X.; Soballe, K. Ceramic bone graft substitute with equine bone protein extract is comparable to allograft in terms of implant fixation: a study in dogs. Acta Orthopaedica 2008, 79 (6), 841-50.

Benzel, E. C.; Thammavaram, K.; Kesterson, L. The diagnosis of infections associated with acrylic cranioplasties. Neuroradiology 1990, 32 (2), 151-3.

Bhumiratana, S.; Grayson, W. L.; Castaneda, A.; Rockwood, D. N.; Gil, E. S.; Kaplan, D. L.; Vunjak-Novakovic, G. Nucleation and growth of mineralized bone matrix on silk-hydroxyapatite composite scaffolds. Biomaterials 2011, 32 (11), 2812-20.

Breeze, J.; Gibbons, A. J.; Shieff, C.; Banfield, G.; Bryant, D. G.; Midwinter, M. J. Combat-related craniofacial and cervical injuries: a 5-year review from the British military. J. Trauma 2011, 71 (1), 108-13.

Broyles, J. M.; Abt, N. B.; Shridharani, S. M.; Bojovic, B.; Rodriguez, E. D.; Dorafshar, A. H. The fusion of craniofacial reconstruction and microsurgery: a functional and aesthetic approach. Plast. Reconstr. Surg. 2014, 134 (4), 760-9.

Brydone, A. S.; Meek, D.; Maclaine, S. Bone grafting, orthopaedic biomaterials, and the clinical need for bone engineering. Proc. Inst. Mech. Eng., Part H 2011, 224 (12), 1329-43.

Correia, C.; Grayson, W. L.; Park, M.; Hutton, D.; Zhou, B.; Guo, X. E.; Niklason, L.; Sousa, R. A.; Reis, R. L.; Vunjak-Novakovic, G. In vitro model of vascularized bone: synergizing vascular development and osteogenesis. PLoS One 2011, 6 (12), e28352.

Cowan, C. M.; Shi, Y. Y.; Aalami, O. O.; Chou, Y. F.; Mari, C.; Thomas, R.; Quarto, N.; Contag, C. H.; Wu, B.; Longaker, M. T. Adipose-derived adult stromal cells heal critical-size mouse calvarial defects. Nat. Biotechnol. 2004, 22 (5), 560-7.

Dalby, M. J.; Gadegaard, N.; Tare, R.; Andar, A.; Riehle, M. O.; Herzyk, P.; Wilkinson, C. D.; Oreffo, R. 0. The control of human mesenchymal cell differentiation using nanoscale symmetry and disorder. Nat. Mater. 2007, 6 (12), 997-1003.

Deligianni, D. D.; Katsala, N. D.; Koutsoukos, P. G.; Missirlis, Y. F. Effect of surface roughness of hydroxyapatite on human bone marrow cell adhesion, proliferation, differentiation and detachment strength. Biomaterials 2001, 22 (1), 87-96.

Desai, B. M. Osteobiologics. Am. J. Orthop. 2007, 36 (4 Suppl), 8-11.

Eshraghi, S.; Das, S. Mechanical and microstructural properties of polycaprolactone scaffolds with one-dimensional, two-dimensional, and three-dimensional orthogonally oriented porous architectures produced by selective laser sintering. Acta Biomater. 2010, 6 (7), 2467-76.

Estes, B. T.; Diekman, B. O.; Gimble, J. M.; Guilak, F. Isolation of adipose-derived stem cells and their induction to a chondrogenic phenotype. Nat. Protoc. 2010, 5 (7), 1294-1311.

Feuerstein, T. J.; Limberger, N. Mathematical analysis of the control of neurotransmitter release by presynaptic receptors as a supplement to experimental data. Naunyn-Schmiedeberg's Arch. Pharmacol. 1999, 359 (5), 345-59.

Gerhardt, L. C.; Widdows, K. L.; Erol, M. M.; Nandakumar, A.; Rogan, I. S.; Ansari, T.; Boccaccini, A. R. Neocellularization and neovascularization of nanosized bioactive glass-coated decellularized trabecular bone scaffolds. J. Biomed. Mater. Res., Part A 2013, 101 (3), 827-41.

Goldstein, S. A. The mechanical properties of trabecular bone: dependence on anatomic location and function. J. Biomech. 1987, 20 (11-12), 1055-61.

Grayson, W. L.; Frohlich, M.; Yeager, K.; Bhumiratana, S.; Chan, M. E.; Cannizzaro, C.; Wan, L. Q.; Liu, X. S.; Guo, X. E.; Vunjak-Novakovic, G. Engineering anatomically shaped human bone grafts. Proc. Natl. Acad. Sci. U.S.A. 2010, 107 (8), 3299-304.

Gupta, D. M.; Kwan, M. D.; Slater, B. J.; Wan, D. C.; Longaker, M. T. Applications of an athymic nude mouse model of nonhealing critical-sized calvarial defects. J. Craniofac. Surg. 2008, 19 (1), 192-7.

Harakas, N. K. Demineralized bone-matrix-induced osteogenesis. Clin. Orthop. Relat. Res. 1984, No. 188, 239-51.

Hung, B. P.; Babalola, O. M.; Bonassar, L. J. Quantitative characterization of mesenchymal stem cell adhesion to the articular cartilage surface. J. Biomed. Mater. Res., Part A 2013, 101 (12), 3592-8.

Hung, B. P.; Hutton, D. L.; Grayson, W. L. Mechanical control of tissue-engineered bone. Stem Cell Res. Ther. 2013, 4 (1), 10.

Hung, B. P.; Hutton, D. L.; Kozielski, K. L.; Bishop, C. J.; Naved, B.; Green, J. J.; Caplan, A. I.; Gimble, J. M.; Dorafshar, A. H.; Grayson, W. L. Platelet-derived growth factor BB enhances osteogenesis of adipose-derived but not bone marrow-derived mesenchymal stromal/stem cells. Stem Cells 2015, 33 (9), 2773-2784.

Hung, B. P.; Salter, E. K.; Temple, J.; Mundinger, G. S.; Brown, E. N.; Brazio, P.; Rodriguez, E. D.; Grayson, W. L. Engineering bone grafts with enhanced bone marrow and native scaffolds. Cells Tissues Organs 2013, 198 (2), 87-98.

Hutton, D. L.; Kondragunta, R.; Moore, E. M.; Hung, B. P.; Jia, X.; Grayson, W. L. Tumor Necrosis Factor improves vascularization in osteogenic grafts engineered with human adipose-derived stem/stromal cells. PLoS One 2014, 9 (9), e107199.

Iejima, D.; Saito, T.; Uemura, T. A collagen-phosphophoryn sponge as a scaffold for bone tissue engineering. J. Biomater. Sci., Polym. Ed. 2003, 14 (10), 1097-1103.

Inzana, J. A.; Olvera, D.; Fuller, S. M.; Kelly, J. P.; Graeve, O. A.; Schwarz, E. M.; Kates, S. L.; Awad, H. A. 3D printing of composite calcium phosphate and collagen scaffolds for bone regeneration. Biomaterials 2014, 35 (13), 4026-34.

Kister, G.; Cassanas, G.; Bergounhon, M.; Hoarau, D.; Vert, M. Structural characterization and hydrolytic degradation of solid copolymers of D,L-lactide-co-epsilon-caprolactone by Raman spectroscopy. Polymer 2000, 41 (3), 925-932.

Langer, R.; Vacanti, J. P. Tissue engineering. Science 1993, 260 (5110), 920-6.

Mandair, G. S.; Morris, M. D. Contributions of Raman spectroscopy to the understanding of bone strength. BoneKEy Rep. 2015, 4, 620.

Marcos-Campos, I.; Marolt, D.; Petridis, P.; Bhumiratana, S.; Schmidt, D.; Vunjak-Novakovic, G. Bone scaffold architecture modulates the development of mineralized bone matrix by human embryonic stem cells. Biomaterials 2012, 33 (33), 8329-42.

Mauney, J. R.; Jaquiery, C.; Volloch, V.; Heberer, M.; Martin, I.; Kaplan, D. L. In vitro and in vivo evaluation of differentially demineralized cancellous bone scaffolds combined with human bone marrow stromal cells for tissue engineering. Biomaterials 2005, 26(16), 3173-3185.

Mauney, J. R.; Blumberg, J.; Pirun, M.; Volloch, V.; Vunjak-Novakovic, G.; Kaplan, D. L. Osteogenic differentiation of human bone marrow stromal cells on partially demineralized bone scaffolds in vitro. Tissue Eng. 2004, 10 (1-2), 81-92.

McNamara, L. E.; McMurray, R. J.; Biggs, M. J.; Kantawong, F.; Oreffo, R. O.; Dalby, M. J. Nanotopographical control of stem cell differentiation. J. Tissue Eng. 2010, 2010, 120623.

Nienhuijs, M. E. L.; Walboomers, X. F.; Briest, A.; Merkx, M. A. W.; Stoelinga, P. J. W.; Jansen, J. A. Healing of bone defects in the goat mandible, using COLLOSS (R) E and beta-tricalciumphosphate. J. Biomed. Mater. Res., Part B 2010, 92B (2), 517-524.

Oliveira, J. M.; Silva, S. S.; Malafaya, P. B.; Rodrigues, M. T.; Kotobuki, N.; Hirose, M.; Gomes, M. E.; Mano, J. F.; Ohgushi, H.; Reis, R. L. Macroporous hydroxyapatite scaffolds for bone tissue engineering applications: physicochemical characterization and assessment of rat bone marrow stromal cell viability. J. Biomed. Mater. Res., Part A 2009, 91 (1), 175-86.

Park, H. K.; Dujovny, M.; Agner, C.; Diaz, F. G. Biomechanical properties of calvarium prosthesis. Neurol. Res. 2001, 23 (2-3), 267-76.

Park, S. H.; Park, D. S.; Shin, J. W.; Kang, Y. G.; Kim, H. K.; Yoon, T. R. Scaffolds for bone tissue engineering fabricated from two different materials by the rapid prototyping technique: PCL versus PLGA. J. Mater. Sci.: Mater. Med. 2012, 23 (11), 2671-8.

Parker, S. E.; Mai, C. T.; Canfield, M. A.; Rickard, R.; Wang, Y.; Meyer, R. E.; Anderson, P.; Mason, C. A.; Collins, J. S.; Kirby, R. S.; Correa, A. Updated National Birth Prevalence estimates for selected birth defects in the United States, 2004-2006. Birth Defects Res., Part A, 2010, 88 (12), 1008-16.

Reddy, S.; Khalifian, S.; Flores, J. M.; Bellamy, J.; Manson, P. N.; Rodriguez, E. D.; Dorafshar, A. H. Clinical outcomes in cranioplasty: risk factors and choice of reconstructive material. Plast. Reconstr. Surg. 2014, 133 (4), 864-73.

Reyes, C. D.; Garcia, A. J. A centrifugation cell adhesion assay for high-throughput screening of biomaterial surfaces. J. Biomed. Mater. Res., Part A 2003, 67 (1), 328-33.

Saito, E.; Liao, E. E.; Hu, W. W.; Krebsbach, P. H.; Hollister, S. J. Effects of designed PLLA and 50:50 PLGA scaffold architectures on bone formation in vivo. J. Tissue Eng. Regener. Med. 2013, 7 (2), 99-111.

Sampath, T. K.; Reddi, A. H. Dissociative extraction and reconstitution of extracellular matrix components involved in local bone differentiation. Proc. Natl. Acad. Sci. U.S.A. 1981, 78 (12), 7599-603.

Sathyavathi, R.; Saha, A.; Soares, J. S.; Spegazzini, N.; McGee, S.; Rao Dasari, R.; Fitzmaurice, M.; Barman, I. Raman spectroscopic sensing of carbonate intercalation in breast microcalcifications at stereotactic biopsy. Sci. Rep. 2015, 5, 9907.

Sauermann, W.; Feuerstein, T. J. Some mathematical models for concentration-response relationships. Biom. J. 1998, 40 (7), 865-881.

Sawyer, A. A.; Song, S. J.; Susanto, E.; Chuan, P.; Lam, C. X. F.; Woodruff, M. A.; Hutmacher, D. W.; Cool, S. M. The stimulation of healing within a rat calvarial defect by mPCL-TCP/collagen scaffolds loaded with rhBMP-2. Biomaterials 2009, 30 (13), 2479-2488.

Stoppato, M.; Carletti, E.; Sidarovich, V.; Quattrone, A.; Unger, R. E.; Kirkpatrick, C. J.; Migliaresi, C.; Motta, A. Influence of scaffold pore size on collagen I development: A new in vitro evaluation perspective. J. Bioact. Compat. Polym. 2013, 28 (1), 16-32.

Suwanprateeb, J.; Sanngam, R.; Suvannapruk, W.; Panyathanmaporn, T. Mechanical and in vitro performance of apatite-wollastonite glass ceramic reinforced hydroxyapatite composite fabricated by 3D-printing. J. Mater. Sci.: Mater. Med. 2009, 20 (6), 1281-1289.

Taddei, P.; Tinti, A.; Reggiani, M.; Fagnano, C. In vitro mineralization of bioresorbable poly(epsilon-caprolactone)/apatite composites for bone tissue engineering: a vibrational and thermal investigation. J. Mol. Struct. 2005, 744, 135-143.

Temple, J. P.; Hutton, D. L.; Hung, B. P.; Huri, P. Y.; Cook, C. A.; Kondragunta, R.; Jia, X. F.; Grayson, W. L. Engineering anatomically shaped vascularized bone grafts with hASCs and 3Dprinted PCL scaffolds. J. Biomed. Mater. Res., Part A 2014, 102 (12), 4317-4325.

Ucar, S.; Yilgor, P.; Hasirci, V.; Hasirci, N. Chitosan-based wetspun scaffolds for bioactive agent delivery. J. Appl. Polym. Sci. 2013, 130 (5), 3759-3769.

Umeda, H.; Kanemaru, S.; Yamashita, M.; Kishimoto, M.; Tamura, Y.; Nakamura, T.; Omori, K.; Hirano, S.; Ito, J. Bone regeneration of canine skull using bone marrow-derived stromal cells and beta-tricalcium phosphate. Laryngoscope 2007, 117 (6), 997-1003.

Urist, M. R. Bone: formation by autoinduction. Science 1965, 150 (3698), 893-9.

Urist, M. R.; Mikulski, A.; Lietze, A. Solubilized and insolubilized bone morphogenetic protein. Proc. Natl. Acad. Sci. U.S.A. 1979, 76 (4), 1828-32.

Wang, Y. K.; Yu, X.; Cohen, D. M.; Wozniak, M. A.; Yang, M. T.; Gao, L.; Eyckmans, J.; Chen, C. S. Bone morphogenetic protein-2-induced signaling and osteogenesis is regulated by cell shape, RhoA/ROCK, and cytoskeletal tension. Stem Cells Dev. 2012, 21 (7), 1176-1186.

Wei, F. C.; Seah, C. S.; Tsai, Y. C.; Liu, S. J.; Tsai, M. S. Fibula osteoseptocutaneous flap for reconstruction of composite mandibular defects. Plast. Reconstr. Surg. 1994, 93 (2), 294-304.

Yilgor, P.; Hasirci, N.; Hasirci, V. Sequential BMP-2/BMP-7 delivery from polyester nanocapsules. J. Biomed. Mater. Res., Part A 2010, 93 (2), 528-36.

Zein, I.; Hutmacher, D. W.; Tan, K. C.; Teoh, S. H. Fused deposition modeling of novel scaffold architectures for tissue engineering applications. Biomaterials 2002, 23 (4), 1169-85.

Zhou, Y. F.; Hutmacher, D. W.; Varawan, S. L.; Lim, T. M. In vitro bone engineering based on polycaprolactone and polycaprolactone-tricalcium phosphate composites. Polym. Int. 2007, 56 (3), 333-342.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A three-dimensional (3D) printed porous extracellular matrix (ECM) scaffold comprising:
    a 3D printable ECM mixture comprising 30% by weight of ECM material having a particle size less than 40 pm and 70% by weight of a biocompatible synthetic polymer material, wherein the biocompatible synthetic polymer material comprises poly(ε-caprolactone) (PCL), and wherein the ECM material comprises a mineral phase and a collagen phase of decellularized bone; and
    wherein the 3D printed porous ECM scaffold has a plurality of human adipose-derived stem cells (hASCs) seeded thereto.

2. The 3D printed porous ECM scaffold of claim 1, wherein the ECM material comprises a material selected from the group consisting of trabecular bone, cortical bone, connective tissue, and combinations thereof.

3. The 3D printed porous ECM scaffold of claim 1, wherein the mineral phase of the ECM material comprises a degree of mineralization selected from the group consisting of fully mineralized, partially mineralized, demineralized, and combinations thereof.

4. The three-dimensional (3D) printed porous ECM scaffold of claim 1 wherein the scaffold comprises a pore size of 800 μm.

5. The three-dimensional (3D) printed porous ECM scaffold of claim 1, wherein the scaffold has a porosity of 60%.

6. The three-dimensional (3D) printed porous ECM scaffold of claim 1, wherein the scaffold has a root-mean-square roughness value having a range from 40 nm to 60 nm.

7. The three-dimensional (3D) printed porous ECM scaffold of claim 6, wherein the scaffold has a root-mean-square roughness value of 50 nm.

8. The three-dimensional (3D) printed porous ECM scaffold of claim 1, wherein the scaffold comprises a three-dimensional printed lattice structure.

9. The 3D printed ECM scaffold of claim 1, wherein the scaffold comprises an anatomical shape.

10. A method of making a porous extracellular matrix (ECM) scaffold, the method comprising:
    (a) providing a 3D printable extracellular matrix (ECM) mixture comprising 30% by weight of ECM material having a particle size less than 40 pm and from 70% by weight of a biocompatible synthetic polymer material, wherein the biocompatible synthetic polymer material comprises poly(ε-caprolactone) (PCL), and wherein the ECM material comprises a mineral phase and a collagen phase of decellularized bone;
    (b) printing the porous ECM scaffold with a 3D printing process; and
    (c) seeding the 3D-printed porous ECM scaffold with a plurality of human adipose-derived stem cells (hASCs).

11. The method of claim 10, wherein the ECM mixture is in a form selected from the group consisting of a pellet, a powder, a solution, and filament.

12. The method of claim 10, wherein the 3D printing process is selected from the group consisting of vat photopolymerisation, material jetting, binder jetting, fused deposition modelling, powder bed fusion, sheet lamination, and directed energy deposition.

13. The method of claim 10, further comprising:
    (a) obtaining a tomography image of a subject's anatomical bone or organ; and
    (b) using the tomography image of step (a) to inform the 3D printing process to form an anatomically-shaped porous ECM scaffold.

14. A three-dimensional (3D) printed porous ECM scaffold fabricated by the method of claim 10.

15. The 3D printed porous ECM scaffold of claim 14, wherein the scaffold has an anatomical shape.

* * * * *

UNITED STATES PATENT AND TRADEMARK OFFICE
CERTIFICATE OF CORRECTION

| | |
|---|---|
| PATENT NO. | : 11,925,725 B2 |
| APPLICATION NO. | : 15/739946 |
| DATED | : March 12, 2024 |
| INVENTOR(S) | : Warren Grayson |

It is certified that error appears in the above-identified patent and that said Letters Patent is hereby corrected as shown below:

On the Title Page

Item (73) Assignee, Please change "JOHNS HOPKINS UNIVERSITY" to --THE JOHNS HOPKINS UNIVERSITY--.

Signed and Sealed this
Thirtieth Day of April, 2024

Katherine Kelly Vidal
*Director of the United States Patent and Trademark Office*